United States Patent
Hirschel et al.

(10) Patent No.: US 10,350,356 B2
(45) Date of Patent: Jul. 16, 2019

(54) AUTOINJECTOR WITH A SIGNALING DEVICE

(71) Applicant: TecPharma Licensing AG, Burgdorf (CH)

(72) Inventors: Jürg Hirschel, Bern (CH); Markus Tschirren, Burgdorf (CH); Ulrich Moser, Heimiswil (CH); Ursina Streit, Schönbühl (CH)

(73) Assignee: TecPharma Licensing AG, Burgdorf (CH)

( * ) Notice: Subject to any disclaimer, the term of this patent is extended or adjusted under 35 U.S.C. 154(b) by 262 days.

(21) Appl. No.: 14/858,790

(22) Filed: Sep. 18, 2015

(65) Prior Publication Data

US 2016/0008542 A1    Jan. 14, 2016

Related U.S. Application Data

(63) Continuation of application No. PCT/CH2014/000035, filed on Mar. 20, 2014.

(30) Foreign Application Priority Data

Mar. 22, 2013 (EP) .................................... 13160614
Jul. 31, 2013 (EP) .................................... 13178676

(51) Int. Cl.
*A61M 5/20* (2006.01)
*A61M 5/315* (2006.01)
(Continued)

(52) U.S. Cl.
CPC ........ *A61M 5/2033* (2013.01); *A61M 5/3157* (2013.01); *A61M 5/3129* (2013.01);
(Continued)

(58) Field of Classification Search
CPC .......... A61M 5/3157; A61M 2205/581; A61M 5/2033; A61M 5/20; A61M 5/3129; A61M 2005/3143; A61M 5/31565
See application file for complete search history.

(56) References Cited

U.S. PATENT DOCUMENTS

2008/0262438 A1   10/2008  Bollenbach et al.
2010/0036320 A1   2/2010   Cox et al.
(Continued)

FOREIGN PATENT DOCUMENTS

DE         10359694          7/2005
DE    102007013836 A1         9/2008
(Continued)

OTHER PUBLICATIONS

International Search Report dated Jun. 25, 2014, for International Application No. PCT/CH2014/000035, 2 pages.
(Continued)

*Primary Examiner* — Bradley J Osinski
*Assistant Examiner* — Nilay Shah
(74) *Attorney, Agent, or Firm* — Dorsey & Whitney LLP

(57) ABSTRACT

An autoinjector for dispensing a liquid product includes a housing; a product container arranged in the housing, particularly, a syringe comprising a displaceable piston; a drive member; a first spring which acts on the drive member and the piston to dispense the product from the container; a signal element releasably axially coupled with the drive member so that the signal element is transported in the dispensing direction as the drive member is displaced; and a second spring, which exerts a spring force on the signal element against the dispensing direction and is tensioned as the signal element is transported in the dispensing direction. When the signal element is released or detached from the axial coupling, the second spring causes the signal element
(Continued)

to accelerate opposite the dispensing direction and strike against a signal stop and generate an acoustic and/or tactile signal.

19 Claims, 15 Drawing Sheets

(51) Int. Cl.
*A61M 5/31* (2006.01)
*A61M 5/32* (2006.01)

(52) U.S. Cl.
CPC ... *A61M 5/3204* (2013.01); *A61M 2005/2013* (2013.01); *A61M 2005/3109* (2013.01); *A61M 2205/581* (2013.01); *A61M 2205/582* (2013.01)

(56) References Cited

U.S. PATENT DOCUMENTS

2010/0137798 A1 6/2010 Streit et al.
2011/0196339 A1 8/2011 Hirschel et al.
2011/0218500 A1 9/2011 Grunhut et al.
2016/0008541 A1 1/2016 Hirschel et al.

FOREIGN PATENT DOCUMENTS

| DE | 102008037310 | | 7/2010 | |
|----|---|---|---|---|
| EP | 2489380 | | 8/2012 | |
| EP | 2489380 A1 | * | 8/2012 | .......... A61M 5/3158 |
| JP | 2008229344 A | | 10/2008 | |
| WO | 9411041 A1 | | 5/1994 | |
| WO | WO 2004/047892 | | 6/2004 | |
| WO | WO 2010/017650 | | 2/2010 | |
| WO | WO 2011/043714 | | 4/2011 | |
| WO | 2011123024 A1 | | 10/2011 | |
| WO | 2012110577 A1 | | 8/2012 | |
| WO | 2012117255 A1 | | 9/2012 | |
| WO | 2013016832 A1 | | 2/2013 | |

OTHER PUBLICATIONS

"International Search Report" dated Jun. 12, 2014, for International Application No. PCT/CH2014/000034, 3 pages.

* cited by examiner

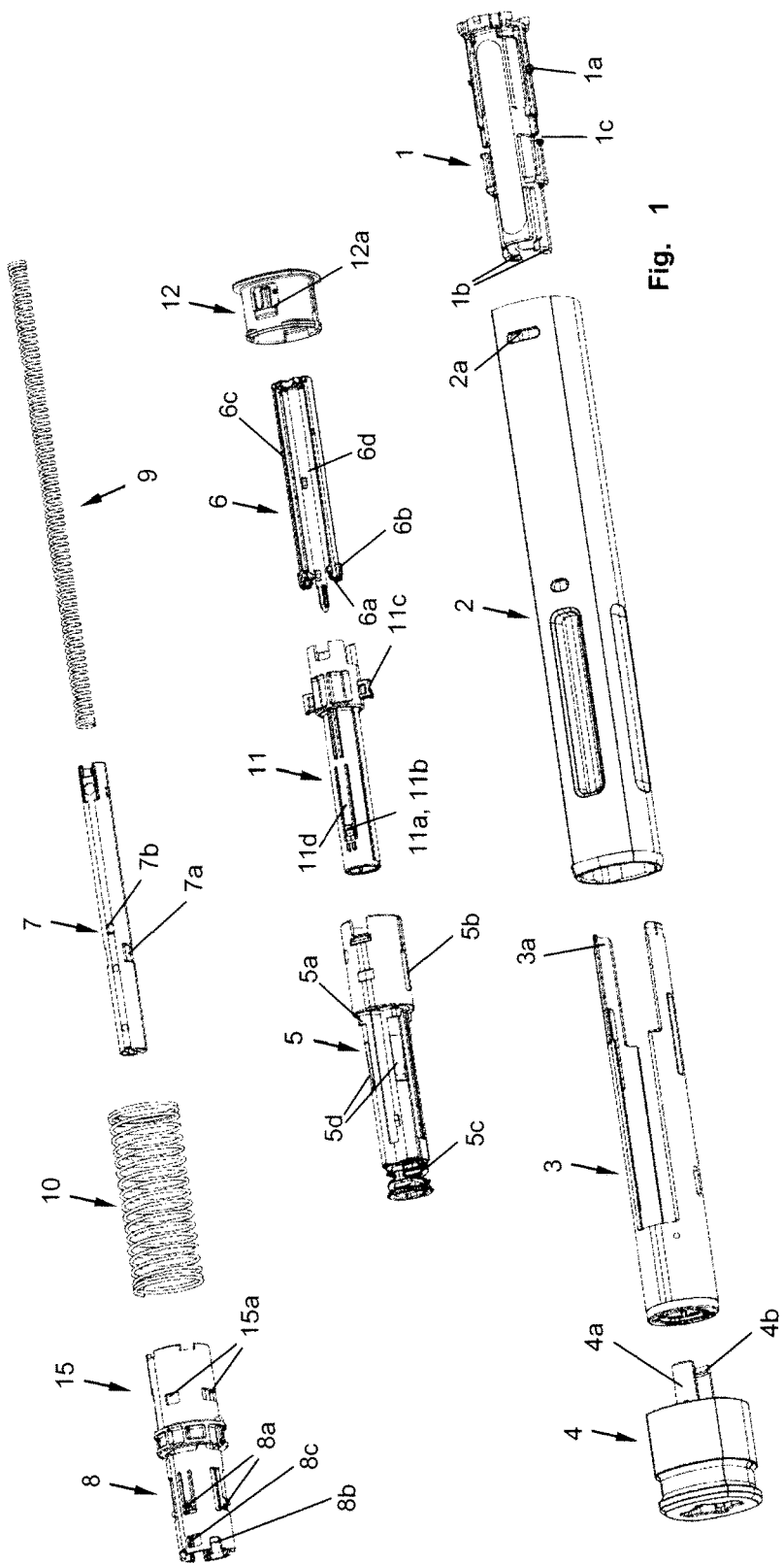

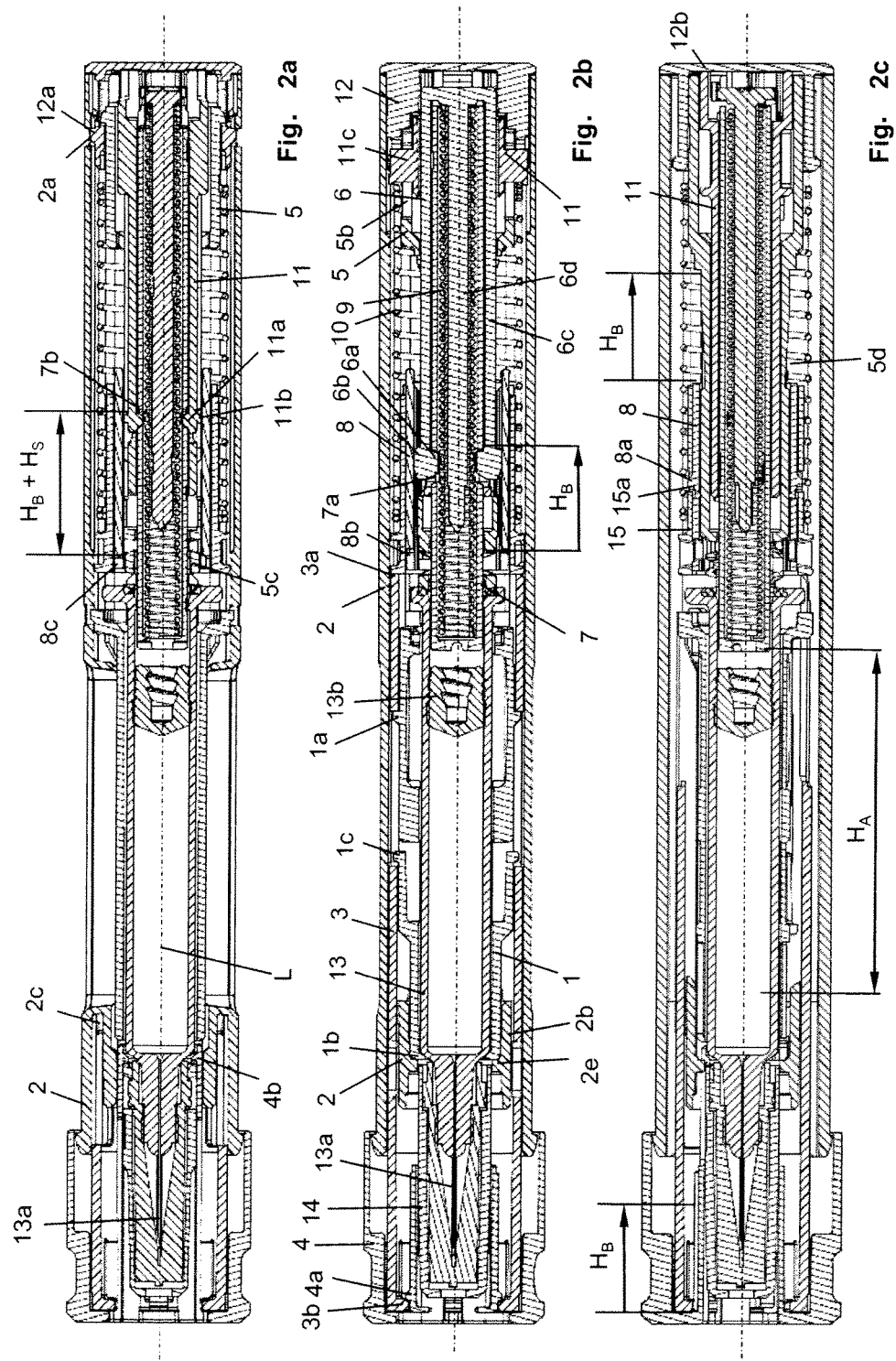

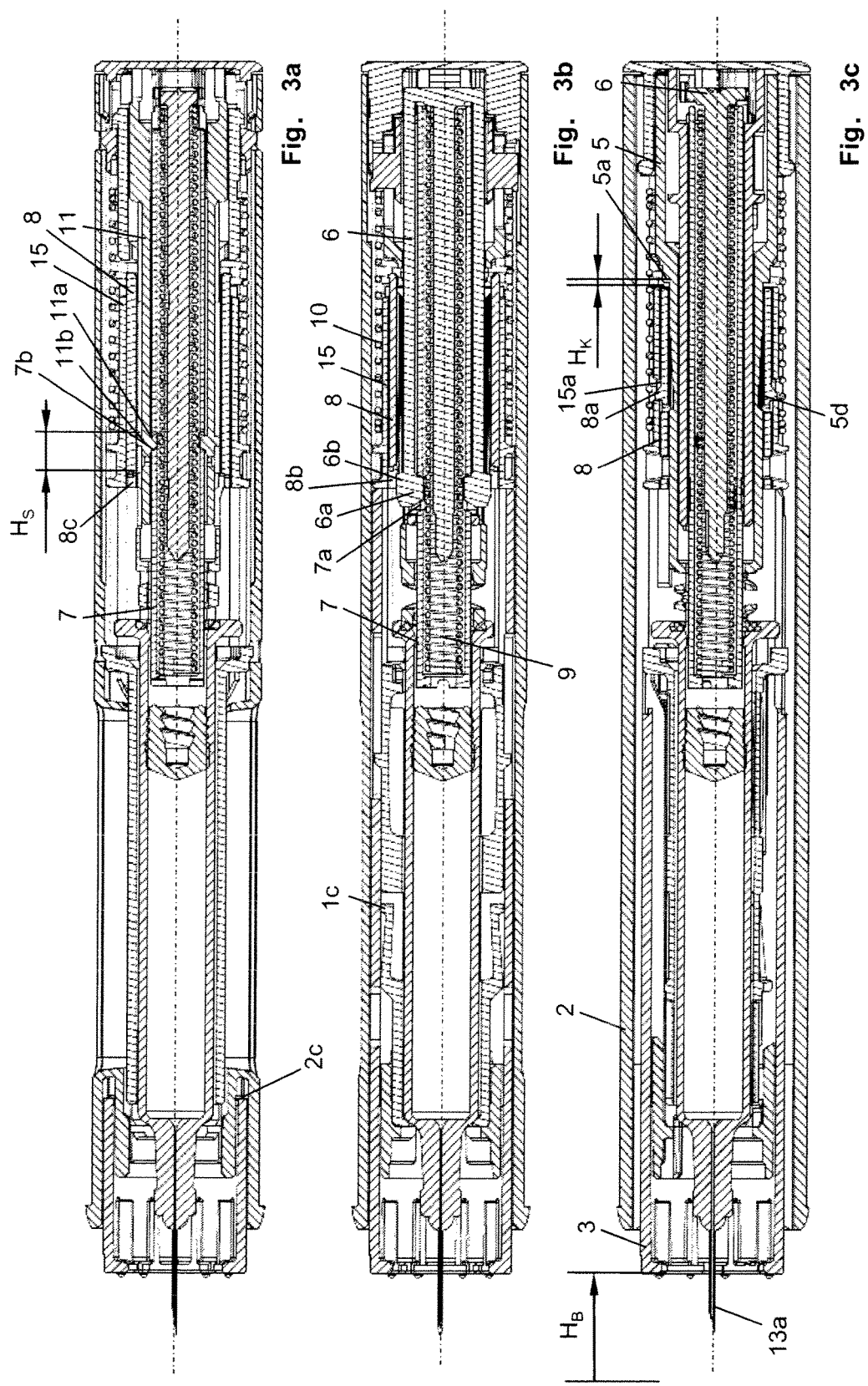

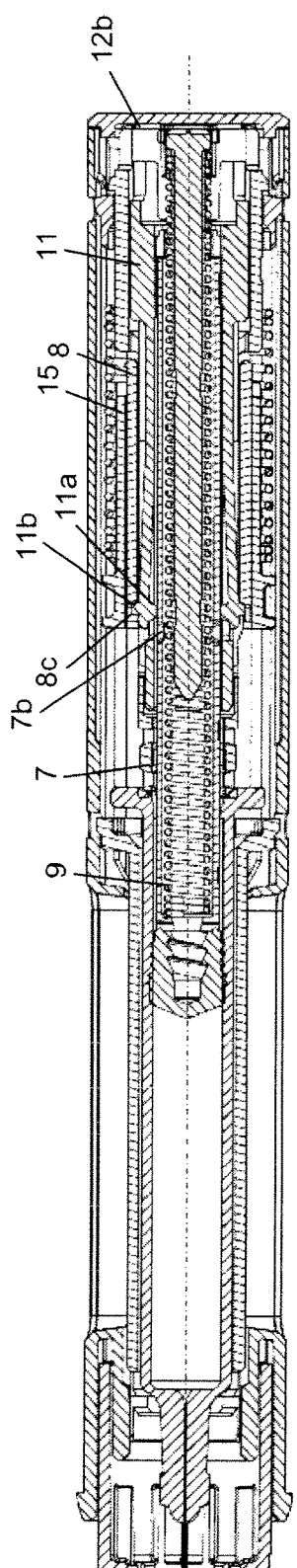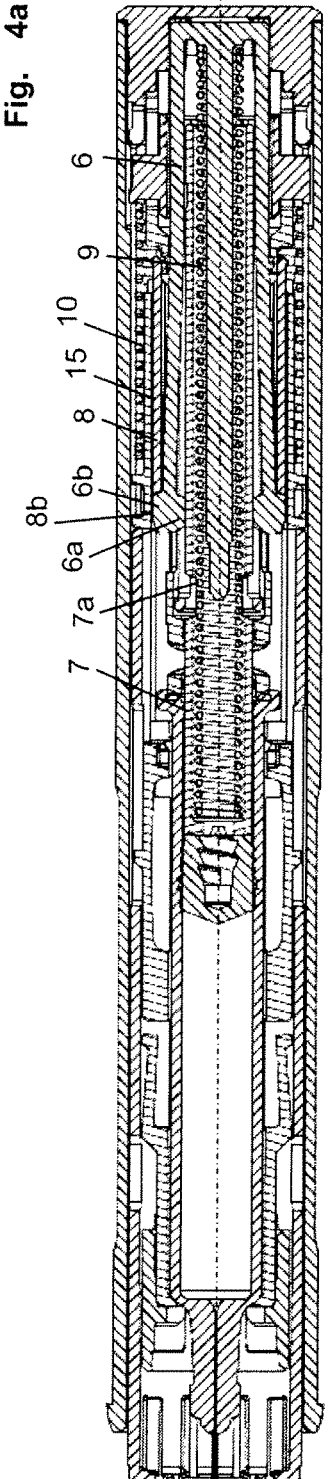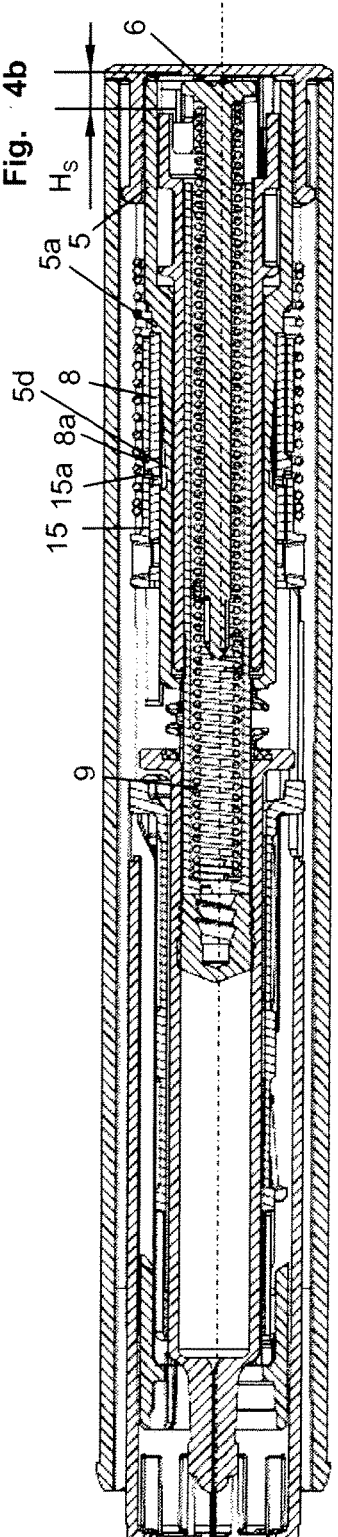

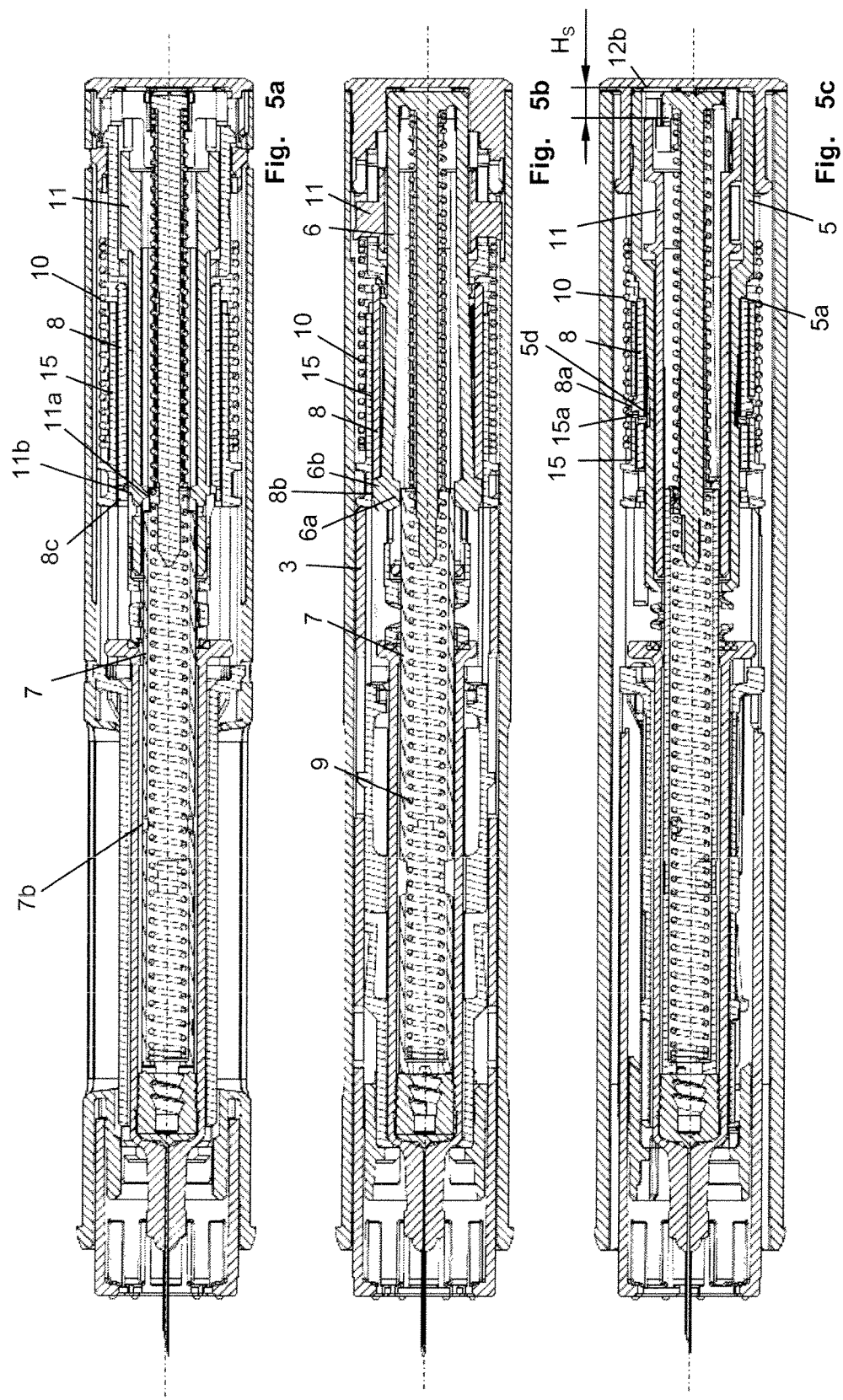

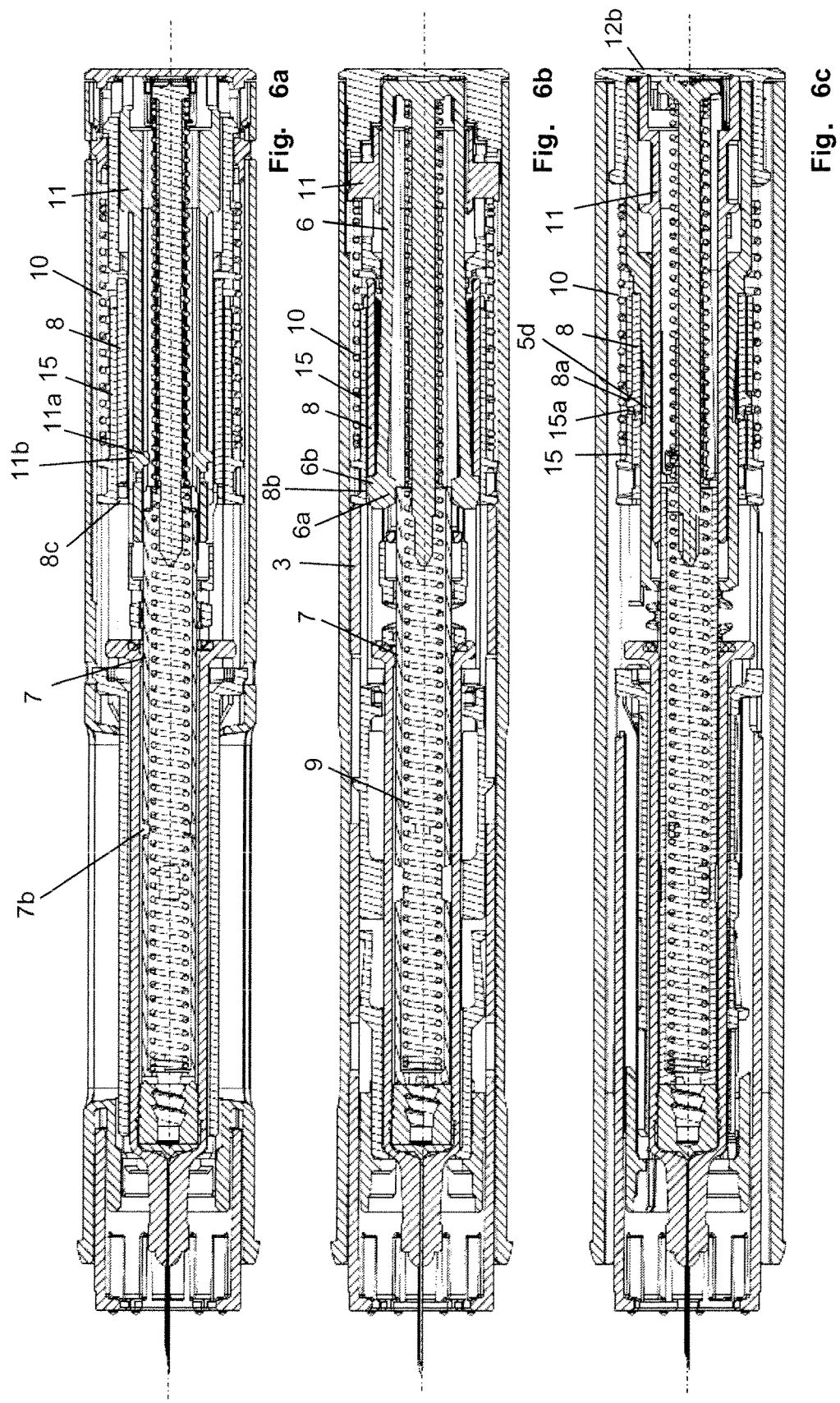

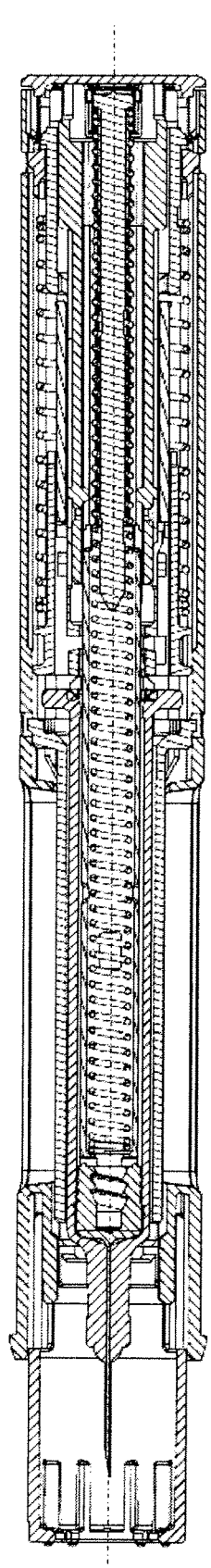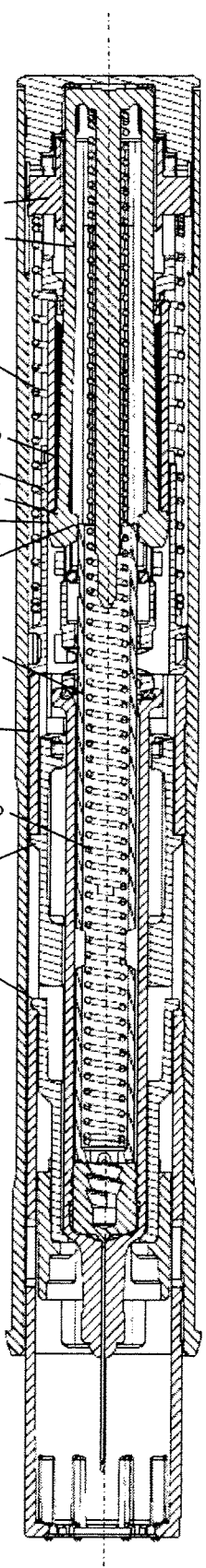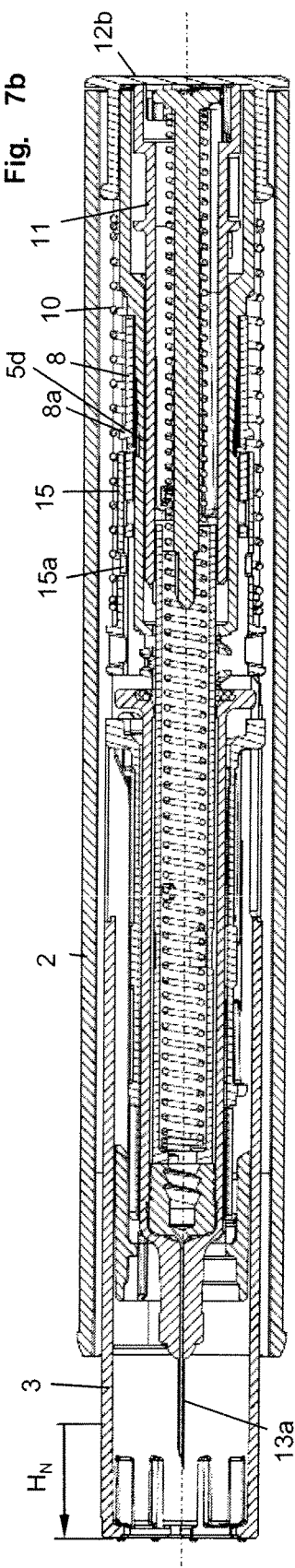

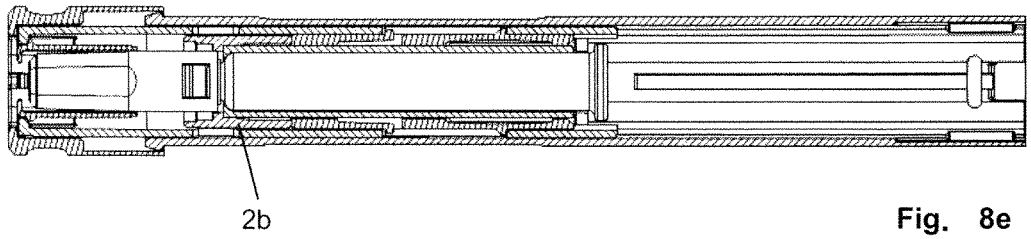
2b    Fig. 8e
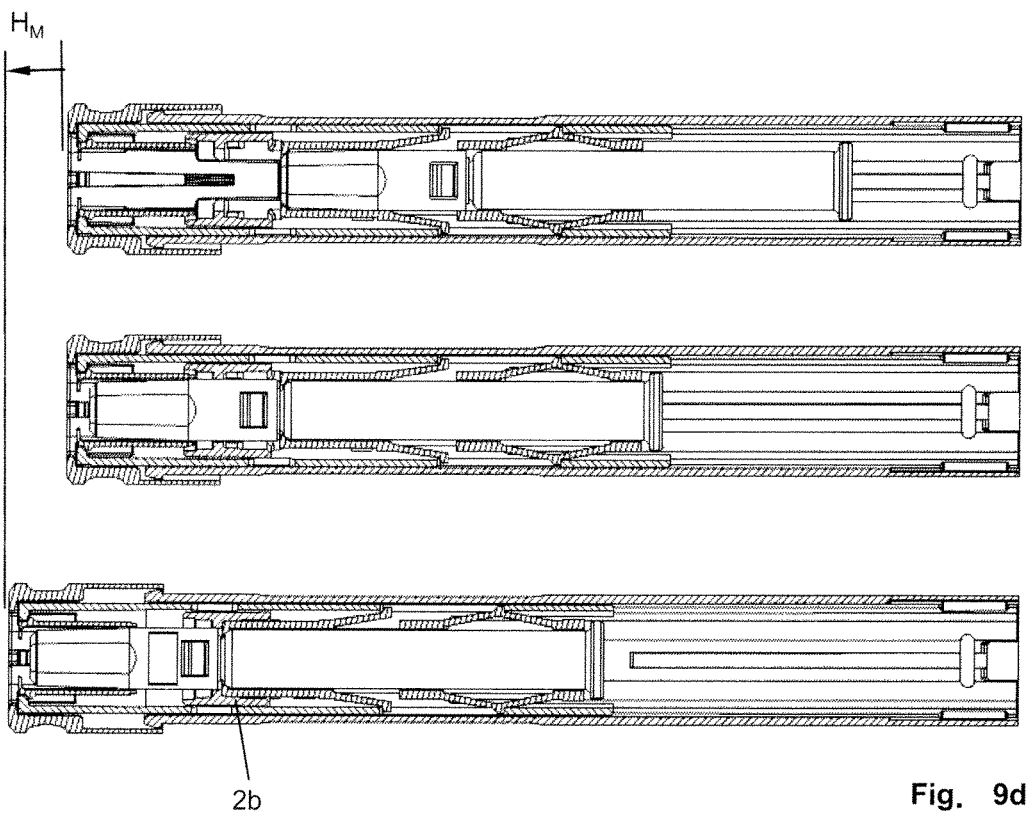
$H_M$
2b    Fig. 9d

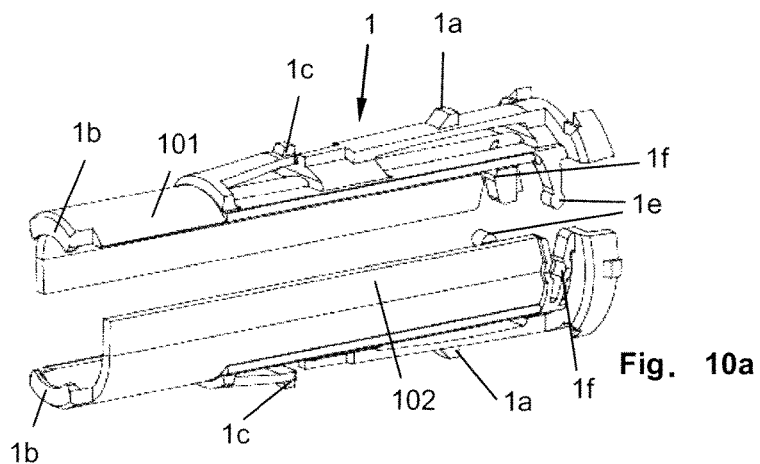
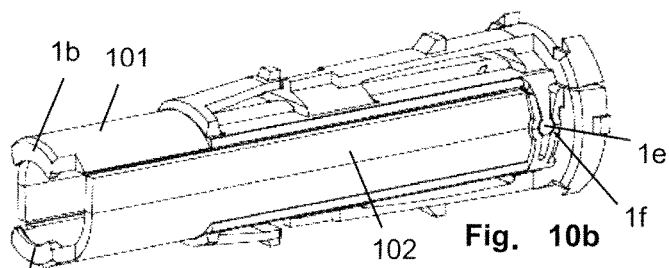
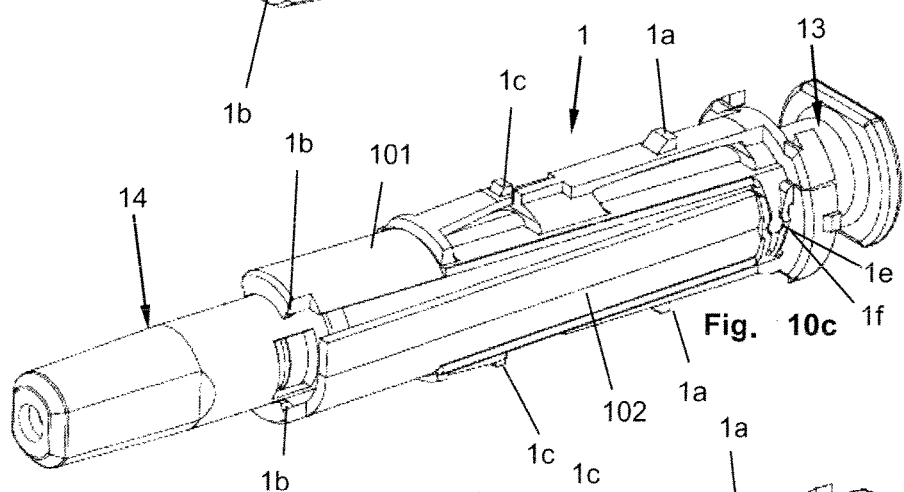
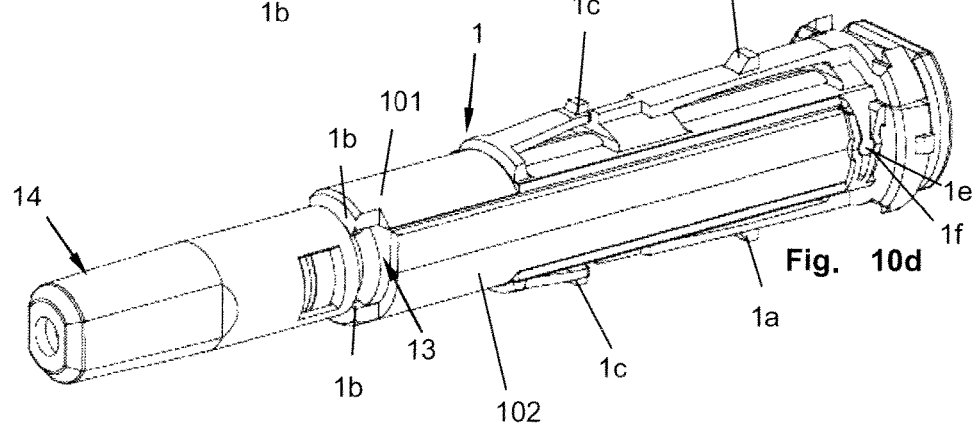

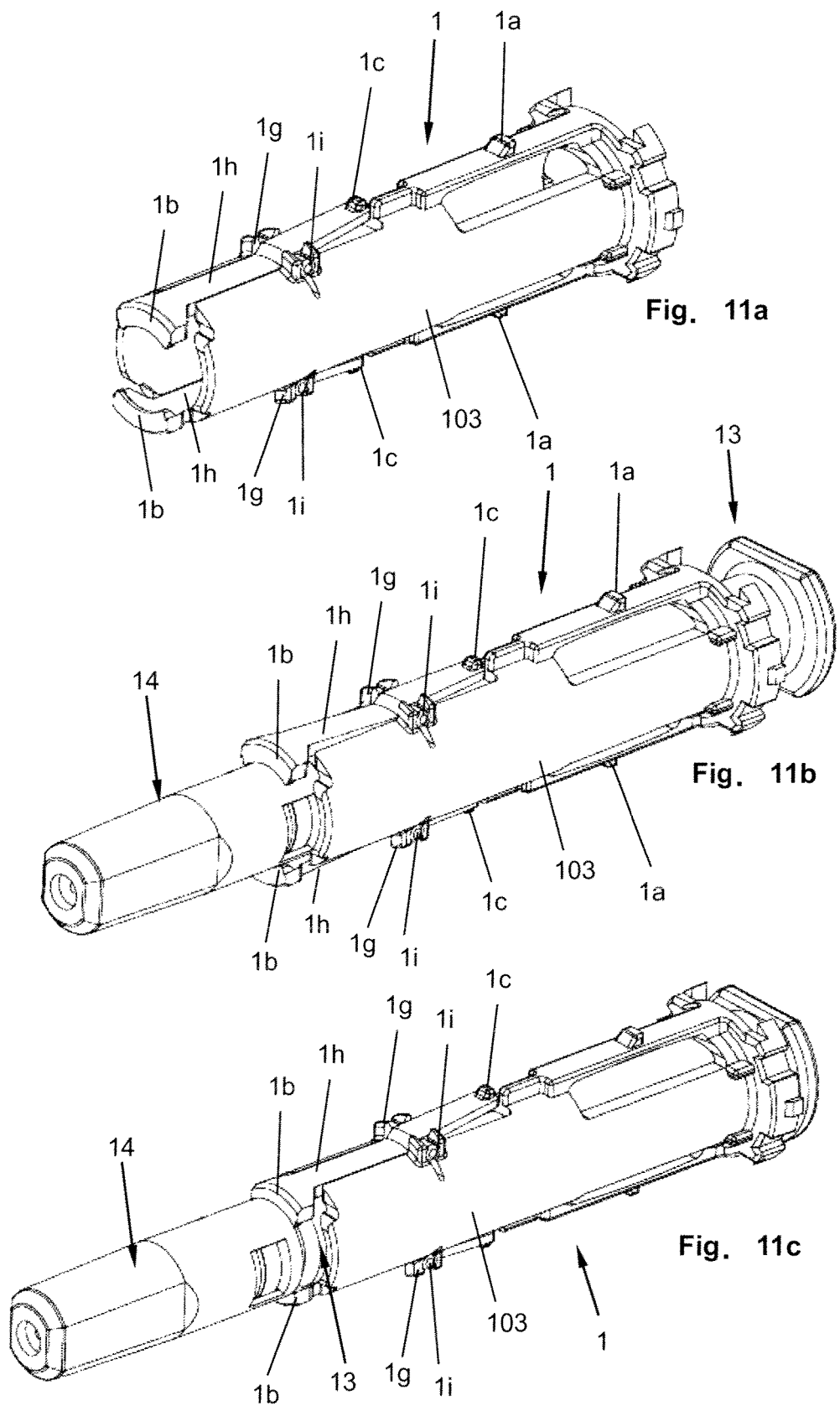

AUTOINJECTOR WITH A SIGNALING DEVICE

CROSS-REFERENCE TO RELATED APPLICATIONS

This application is a Continuation of International Patent Application No. PCT/CH2014/000035 filed Mar. 20, 2014, which claims priority to European Patent Application No. 13160614.7 filed Mar. 22, 2013 and European Patent Application No. 13178676.6 filed Jul. 31, 2013, the entire contents of each are incorporated herein by reference.

TECHNICAL FIELD

The invention relates to an autoinjector, which is also often referred to as an autoinjection device, with which a product contained in a product container is automatically dispensed following a trigger release. The liquid product is, in particular, a medication. The invention particularly relates to a signaling device that generates an acoustic or tactile signal at the end of product dispensing in order to inform the user as to the end of the completed product dispension.

BACKGROUND

Autoinjectors are known in the art. Devices are also known which signal the end of product dispension. An injection device is known from DE 102008037310 A1 and WO 2010/017650 A1 which has a spring element on the piston rod that, at the end of the automatic dispensing, radially snaps over ribs on the housing and produces the so-called "end click."

Injection devices, in particular, autoinjectors are further known from DE 10359694 A1 and WO 2004/047892 A1, having a needle protective sleeve which is supported on a needle protective spring that is not tensed. During the automatic injection procedure with the needle, the needle protective spring is tensed. After removal of the injection device from the injection site, the spring, which is now tensed, can now push the needle protective sleeve over the needle tip in distal direction.

SUMMARY

An object of the invention is to provide an autoinjector having a device for generating an acoustic and/or tactile signal, with a low-cost and operationally reliable design of the autoinjector.

The object is achieved with the autoinjector according to the independent claims with advantageous further developments arising from the dependent claims, the description, and the figures.

The autoinjector according to the invention has a housing and a product container arranged in the housing. The product container can be, in particular, a syringe having a syringe body, on the distal end of which an injection needle is fixedly arranged. The preferably cylindrical syringe body surrounds a piston that is moveable relative to the syringe body and is pushed in the direction of the distal end for dispensing the product, whereby the liquid product, in particular, a medication, that is located between the piston and the injection needle is dispensed from the product container through the injection needle. The syringe body may comprise a flange, which may also be referred to as a finger flange, on its proximal end, e.g., end opposite the injection needle. A syringe formed in this way is available as a standard syringe, so that there is no specific requirement to develop a specially adapted syringe for the autoinjector. The piston is sealingly arranged against the inside diameter of the syringe body.

The housing is preferably elongated and forms the longitudinal axis of the autoinjector. The housing preferably has the shape of a sleeve and/or is cylindrical, in particular, circular cylindrical. The product container is arranged in the housing. For example, the container can be slideably arranged in the housing, i.e., slideable in the distal direction relative to the housing for automatic injection, so that the needle tip protrudes from an opening on the distal end of the autoinjector and can be automatically injected into the patient. Optionally, with such a device the needle tip can be moved after product dispensing into the distal end of the device, in particular, the product container can be moved in the proximal direction relative to the housing.

In preferred embodiments, the product container is accommodated in the housing so it cannot be moved along the longitudinal axis, in particular, by means of a product container holder or a syringe holder that holds the product in an axially fixed manner and is also connected with the housing in an axially fixed manner, in particular, in a locking manner. Preferably, the needle tip protrudes over the distal end of the housing in the distal direction. In this way, the needle can be injected into the injection site by means of a movement of the housing toward the patient. Preferably, a needle protective sleeve is provided that forms the distal end of the autoinjector and has an opening for the injection needle that allows the needle to pass through the opening. The needle protective sleeve can be arranged in its starting position relative to the needle tip such that the needle protective sleeve distally protrudes over the needle tip or such that the needle tip protrudes distally over the distal end of the needle protective sleeve. The needle protective sleeve can be moved in the proximal direction relative to the housing by one activation stroke from its starting position into an actuated position, in particular, it can be moved into the housing so that the needle protrudes, or further protrudes, from the distal end and/or through the opening of the needle protective sleeve. Preferably, the needle protective sleeve can be moved in the distal direction relative to the housing by one needle protective stroke from the actuated position into a needle protective position, in which the distal end of the needle protective sleeve protrudes distally over the needle tip after the use of the device is completed and/or after the dispensing of the product is completed in order to prevent or reduce injury risks originating from an exposed needle tip. The needle protective sleeve may, for example, be displaced in the proximal direction, for example, against the force of a spring that may be referred to as the needle protective spring, wherein the spring that is, for example, the second spring described further below or a spring independent thereof, can move the needle protective sleeve from the actuated position in the distal direction, i.e., into the needle protective position. The autoinjector may, for example, comprise an elastically arranged locking element that locks the needle protective sleeve in its needle protective position, in particular, relative to the housing, and blocks a returning of the needle protective sleeve in the proximal direction or into the housing. The locking element locks the needle protective sleeve at least in such a manner that the needle cannot protrude from the distal end of the needle protective sleeve. The needle protective sleeve may, for example, be moved from the needle protective position only to such an extent in the proximal direction that the needle tip does not protrude from the distal end of the needle protective sleeve.

The autoinjector further comprises a drive member that acts on the piston, in particular, rests against the piston, at least during the dispensing of the product and a first spring which acts on the drive member such as, for example, by supporting in particular, its distal end against the drive member. The drive member can, for example, be sleeve-shaped and form a shoulder that is arranged, for example, in the area of the distal end of the drive member against which the distal end of the first spring can be supported. The first spring is preferably arranged within the sleeve-shaped drive member. The spring is preferably a coiled spring which acts as a compression spring and is preferably formed of metal. The first spring is so highly pretensioned, in particular, in the delivery state of the autoinjector, that it and/or the energy stored therein is sufficient to essentially dispense the product completely out of the product container by the movement of the drive member by one dispensing stroke. The movement of the drive member by one dispensing stroke also moves the piston. If a space exists between the piston and the drive member in the delivery state, the dispensing stroke of the piston is smaller than the dispensing stroke of the drive member, which is preferable since the piston is unloaded until used, thus preventing unwanted premature dispensing of the product. In principle, however, it is also possible for the drive member to rest against the piston in the delivery state and not only during the dispensing of the product. If the drive member rests against the piston already in the delivery state, the dispensing stroke of the piston corresponds to the dispensing stroke of the drive member. The proximal end of the first spring, which, due to its function, can also be referred to as the dispensing spring, can be supported against the housing or a stationary element within the housing, in particular, an element that is only temporarily axially fixed relative to the housing.

According to the invention, the autoinjector comprises a signal element, a signal stop, and a second spring. The second spring may exert a spring force on the signal element in a direction opposite the dispensing direction, or a spring force acting in the proximal direction. In particular, the second spring may be supported, for example, with its proximal end, against the signal element.

The second spring may, for example, be a coiled spring acting as a compression spring that is supported with its proximal end against the signal element. The spring can be supported, for example, with its proximal end against the housing or against a stationary element within the housing. It is particularly preferred for the second spring to be supported with its distal end against the needle protective sleeve or against an element which is moveable together with the needle protective sleeve during the movement of the needle protective sleeve relative to the housing. For example, the element can be a switch module or a switch sleeve in the form described further below. The element can be arranged, in particular, kinematically and/or geometrically between the needle protective sleeve and the distal end of the second spring. The advantage hereby is that the needle protective sleeve can be moved from its actuated position into the needle protective position by means of the second spring. The spring can thus preferably fulfill a double function since it also exerts the aforementioned force on the signal element.

Especially in the delivery state or during a first partial stroke of the dispensing stroke of the drive member the signal element can be coupled in an axially fixed manner with the drive member so that the signal element can be moved together with the drive member along the longitudinal axis and in particular, relative to the housing in particular, in the distal direction. The axially fixed coupling with the drive member causes the signal element to be moved in the dispensing direction during the movement of the drive member, in particular, while the first partial stroke of the dispensing stroke is being performed, and the second spring is tensed. During a second partial stroke of the dispensing stroke, it is preferable that the axially fixed coupling between the signal element and the drive member is released. The axially fixed coupling between the signal element and the drive member is thus releasable. When the axially fixed coupling between the signal element and drive member is released—and in particular, no other couplings between the signal element and a further element are present, as described further below—the signal element can be accelerated by means of the second pretensioned spring in a direction opposite the dispensing direction and relative to the drive member and/or the housing. As a result of the signal element being moved together by the first partial stroke by the drive member, a space that extends, for example, along the longitudinal axis, is formed between the signal stop and the signal element that corresponds in particular, to the first partial stroke. The second spring can accelerate the signal element across this space, and thereby the signal element strikes the signal stop at a speed such that an impulse is imparted to the signal element that produces an acoustic (audible) and/or tactile (perceptible) signal.

The signal stop can be formed by the housing or an at least axially fixed element which is preferably non-rotatably connected to the housing. For example, this element can be a closure cap on the proximal end of the housing and/or form the proximal end of the autoinjector. With particular preference, the closure cap can be connected in a form-locking manner or alternatively in a friction- or material-locking manner. Preferably, the element is locked together with the housing. A separate cap has the advantage that the assembly of the device is facilitated with at least some of the components being arranged within the housing via the proximal end, which is subsequently closed with the cap. The cap may form a resonance body if the signal stop is arranged on the cap so that by the design of material thicknesses and cap shapes the audible impression of the acoustic signal can be changed within certain limits.

In preferred embodiments, the signal element comprises a first engagement element that is, in particular, elastically arranged and/or on an elastic arm and which detachably engages in a drive member, in particular, in a recess of the drive member. In this way, the drive member is coupled with the signal element in an axially fixed manner, with the axially fixed coupling between the drive member and the signal element being released when the signal element, in particular, the first engagement element, becomes disengaged or pushed out of engagement with the drive member, in particular, out of the recess of the drive member. In particular, the first engagement element is released from engagement with the drive member at the end of the first partial stroke of the drive member.

Preferably, the signal stop is arranged along the longitudinal axis of the autoinjector such that it is in alignment with the signal element. This makes it possible for the signal element to strike the signal stop during the movement of the autoinjector along the longitudinal axis.

In embodiments with a needle protective sleeve, it is preferable that the needle protective sleeve acts on the second spring, whereby for triggering of the product dispensing the needle protective sleeve is moveable from its starting position relative to the housing and along the longitudinal axis of the autoinjector in the proximal direction, i.e., in a direction opposite the dispensing direction, in particular, by the activation stroke. In this way, the second spring is tensed and preferably the dispensing of the product, in particular, the movement of the drive member in the dispensing direction, is triggered. The needle protective sleeve is thereby preferably moved from its starting position into its actuated position by the activation stroke so that its distal end is pressed against the injection site of the patient, whereby the housing is being moved relative to the needle protective sleeve in the direction of the injection site so the needle protective sleeve carries out the activation stroke relative to the housing. The needle protruding from the distal end of the needle protective sleeve is thereby also injected into the injection site. After the completed dispensing of the product, especially after, for example, a short waiting period, e.g., 3 to 10 seconds after the signal was generated by the signal element, the autoinjector is removed from the injection site whereby the needle protective sleeve is moved from its actuated position into the needle protective position relative to the housing by the needle protective stroke, especially by means of the spring energy stored in the second spring. The removal of the autoinjector from the injection site also causes the needle to retract from the injection site.

In certain embodiments, a switch module can be kinematically arranged between the second spring and the needle protective sleeve, whereby the switch module is transported in the proximal direction by the needle protective sleeve when the needle protective sleeve is moved from its starting position into the proximal direction or into the actuated position and moves the needle protective sleeve in the distal direction when the spring acting on the switch module moves the switch module in the distal direction. The switch module, or a part thereof, such as, e.g., a switch sleeve, can be an integral part of the needle protective sleeve or, for example, be in form-locking connection, such as e.g. snapped on or resting loosely against the needle protective sleeve. The switch module may comprise a single part or several parts, wherein a multipart switch module can comprise at least the switch sleeve and a blocking sleeve. The blocking sleeve is moveable relative to the needle protective sleeve and/or the switch sleeve, for example, along the longitudinal axis. For example, the spring may be supported on the switch sleeve and on the switch sleeve on the needle protective sleeve. It is possible to provide, for example, a unidirectionally acting locking element between the blocking sleeve and the switch sleeve that preferably engages the aforementioned locking element, which locks the needle protective sleeve in its needle protective position, that is formed, for example, by the blocking sleeve and engages in the switch sleeve, in particular, in a recess. The locking element is preferably designed such that during the movement of the switch sleeve relative to the housing in the proximal direction, the switch sleeve moves the blocking sleeve via the locking element into a locking position, in particular, during the movement of the needle protective sleeve from its starting position into an actuated position, and during the movement relative to the housing in the proximal direction, the locking element is moved into a blocking position relative to the blocking sleeve, in particular, during the movement of the needle protective sleeve from its actuated position into the needle protective position, whereby in the blocking position the locking element or another locking element, such as, e.g., the one mentioned further above, blocks a movement of the switch sleeve relative to the blocking sleeve in the proximal direction. This advantageously prevents the needle protective sleeve from being pushed back into the housing from its needle protective position for a renewed release of the needle tip.

For example, the switch sleeve can comprise a first recess into which the locking element of the blocking sleeve detachably engages when the needle protective sleeve is moved from its starting position into its actuated position. The switch sleeve can comprise, for example, a second recess into which the locking element, or optionally the other locking element, engages when the needle protective sleeve is in its needle protective position. The first and second recesses can be arranged at a distance relative to one another along the longitudinal axis that preferably corresponds to approximately the needle protective stroke. Of course, a reversal of the arrangement of recesses and locking element or locking elements is also possible, i.e., the at least one locking element can be formed on the switch sleeve and the at least one recess, i.e., the first recess and optionally the second recess can be formed on the blocking sleeve.

The locking element and optionally the other locking element can be elastically arranged, in particular, each on an elastic arm. Preferably, the switch sleeve can surround and/or guide the blocking sleeve.

In preferred embodiments, the signal element can comprise a second engagement element which is moveable by means of the disengagement movement of the first engagement element with which the first engagement element moves out of the drive element particularly into an axially fixed engagement with the needle protective sleeve or the switch module, in particular, with the blocking sleeve. The first engagement element and the second engagement element are preferably coordinated with one another in such a way that the second engagement element already engages, preferably in an axially fixed manner, in the needle protective sleeve or the switch module when the first engagement element has not yet completely decoupled from engagement with the drive member. This preferably reliably prevents the first engagement element from being released from engagement with the drive member when the second engagement element has not yet engaged with the needle protective sleeve or the switch module. The needle protective sleeve or the switch module, in particular, the blocking sleeve can have, for example, an additional recess into which the second engagement element of the signal element is engaged, for example, for the axially fixed coupling between the signal element and the signal module, in particular, the blocking sleeve or the needle protective sleeve. The drive member can have a recess into which the first engagement element engages for the axially fixed coupling between the drive member and the signal element. Preferably, the first engagement element and the second engagement element are formed on a shared elastic arm, wherein the first engagement element is directed, for example, radially in direction of the longitudinal axis, and the second engagement element is directed, for example, radially, in the direction opposite the longitudinal axis. The first and second engagement elements can be preferably located radially between the drive member and the needle protective sleeve or the switch module, in particular, between the blocking sleeve.

In particular, during the dispensing stroke of the drive member, especially at the end of the first partial stroke, the first engagement element is released from engagement with the drive member and preferably at the same time, the second engagement element becomes engaged with the switch module or the needle protective sleeve, in particular, with a movement transverse to the longitudinal axis. In particular, by its movement into the dispensing direction, the drive member can press the first engagement element out of the recess of the drive member and the second engagement element into the recess of the needle protective sleeve or the switch module, in particular, into the recess of the blocking sleeve.

In particularly preferred embodiments, the needle protective sleeve or the switch module, in particular, the blocking sleeve, can hold the first engagement element in engagement with the recess of the drive member, whereby the recess for the second engagement element is moved in the direction of the second engagement element by the forward movement of the needle protective sleeve from its starting position to its actuated position relative to the longitudinal axis, wherein the recess in the actuated position of the needle protective sleeve, in particular, at the moment the dispensing stroke is released, is arranged at a distance to the second engagement element along the longitudinal axis that corresponds approximately to the first partial stroke of the signal element. The drive member, released for the dispensing stroke by the activation of the needle protective sleeve, can then be moved by the first partial stroke into the dispensing direction. Preferably, the first engagement element is held in engagement with the drive member by the inner circumference of the needle protective sleeve or the switch module, in particular, the blocking sleeve against which the second engagement element is resting. At the end of the first partial stroke the second engagement element is located in the same position relative to the longitudinal axis as the recess allowing the second engagement element to move into its recess and the first engagement element to move out of its recess.

The dispensing stroke of the drive member can comprise, in particular, two phases, namely the first partial stroke and the second partial stroke. During the first partial stroke, the first engagement element is in axially fixed engagement with the drive member, and the second engagement element out of the axially fixed engagement with the needle protective sleeve or the switch module, in particular, the blocking sleeve. During the second partial stroke of the dispensing stroke, the second engagement element is in an axially fixed engagement with the needle protective sleeve or the switch module, in particular, the blocking sleeve, wherein the first engagement element is out of engagement with the drive member, advantageously causing the drive member to be moveable by means of the first spring in the distal direction relative to the signal element, and/or the signal element to not yet be triggered for the emitting of the signal.

It is generally preferred that the drive element can be moved into the distal direction relative to the signal element by means of the first spring, in particular, by the second partial stroke, when the first engagement element is out of engagement with the drive member and the second engagement element is in engagement with the needle protective sleeve or the switch module.

In preferred embodiments, the second engagement element and the recess for the second engagement element can be arranged in the delivery state of the autoinjector along the longitudinal axis at approximately a distance relative to one another that corresponds to approximately the sum of the activation stroke of the needle protective sleeve and the first partial stroke of the drive member, which corresponds approximately to the stroke of the signal element away from the signal stop.

Preferably, the drive member can prevent the second engagement element from moving out of the axially fixed engagement in the needle protective sleeve or the switch module when the drive member moves in the distal direction relative to the signal element, in particular, during the second partial stroke of the drive member. At the end of the dispensing stroke and/or the second partial stroke, the drive member allows the second engagement element to move out of the engagement with the needle protective sleeve or with the switch module. When at the end of the second partial stroke the second engagement element has moved out of its engagement with the needle protective sleeve or the switch module, the second spring accelerates the signal element in a direction opposite the dispensing direction and the signal element strikes the signal stop. Preferably, the second engagement element is held in engagement with the needle protective sleeve or the switch module by the outer circumference of the drive member against which the first engagement element is resting.

In preferred embodiments, the autoinjector may comprise a holding element against which, for example, an end of the first spring, in particular, the proximal end of the first spring, is supported. Alternatively, the spring can be supported with its proximal end against the housing or on a stationary element within the housing. The holding element itself can be fixed to the housing or be moveably arranged relative to the housing. The holding element may comprise a first engagement element that engages in the drive member prior to dispensing of the product, thereby preventing the drive member from moving in the dispensing direction relative to the holding element and/or the housing. The engagement of the first engagement element in the drive member is releasable for the dispensing of the product. When the engagement is released, the drive member is released for movement in the dispensing direction. The first spring can move the drive member relative to the holding element and/or the housing by one dispensing stroke in the direction of dispensing. The drive member can have a recess for the first engagement element of the holding element, with this coupling between the drive member and the holding element being released when the holding element, in particular, the first engagement element, has moved out of engagement with the drive member, in particular, out of the recess of the drive element. In particular, the first engagement element can be released from engagement with the drive member by the needle protective sleeve being moved by the activation stroke from its starting position into the actuated position. For example, the first engagement element can be held in an axially fixed engagement with the drive member by the needle protective sleeve or the switch module, in particular, the blocking sleeve, when the needle protective sleeve is not in its actuated position or in its starting position. For example, an inner circumference of the needle protective sleeve or the switch module, in particular, of the blocking sleeve, can hold the first engagement element in the engagement with the drive member, with, for example, a second engagement element, which is described further below, resting against the inner circumference.

By the movement of the needle protective sleeve into its actuated position, the needle protective sleeve or the switch module, in particular, the blocking sleeve, can allow the first engagement element to move out of engagement with the drive member, in particular, with a movement transverse to the longitudinal axis of the autoinjector. For example, a recess, in particular, for the second engagement element, which is formed on the needle protective sleeve or the switch module, especially on the blocking sleeve, can be arranged relative to the longitudinal axis in the same position as the first and/or the second engagement element so that the first engagement element can move out of engagement with the drive member. For example, the drive member can press the first engagement element out of engagement with the drive member when the needle protective sleeve is in its actuated position.

The first engagement element can, for example, be directed in a radial direction relative to the longitudinal axis and/or be arranged on an elastic arm of the holding element.

As mentioned, the holding element can comprise a second engagement element that by means of the disengagement movement of the first engagement element out of the drive member is moveable into an axially fixed engagement with the needle protective sleeve or with the switch module, in particular, with the blocking sleeve. The second engagement element can be arranged, for example, on the arm on which the first engagement element is arranged and/or, for example, be directed in a radial direction away from the longitudinal axis. The first engagement element and the second engagement element can be coordinated with one another such that the second engagement element already engages in an axially fixed manner in its recess, which is formed by the needle protective sleeve or the switch module, in particular, by the blocking sleeve, when the first engagement element is not yet completely released from the engagement with the drive member. This advantageously achieves that the axially fixed connection between the holding element and the needle protective sleeve or the switch module is established before the axially fixed connection between the holding element and the drive member is released, thus blocking a renewed or further pushing back of the needle protective sleeve.

Especially when the second engagement element is in its recess, the drive member can move in the distal direction relative to the holding element, in particular, as a result of the energy stored in the pretensioned spring. The drive member can prevent the second engagement element from moving out of the axially fixed engagement in the needle protective sleeve or in the switch module, in particular, in the blocking sleeve, when the drive member moves in distal direction relative to the signal element. Preferably, this applies at the end of the dispensing stroke, in particular, also when the second engagement element of the signal element is released from its recess in order to be accelerated by the second spring in a direction opposite the dispensing direction.

Particularly, in embodiments in which the recess for the second engagement element of the holding element is formed by the needle protective sleeve or the switch sleeve, it is preferred that the second engagement element moves out of its recess at the end of the dispensing stroke, so that the needle protective sleeve can be moved out of the actuated position into the needle protective position after administration of the product. For this purpose, the drive member can have a recess into which the first engagement element can move, whereby the second engagement element simultaneously moves out of its recess, in particular, in order to release the movement of the needle protective sleeve in the distal direction.

In embodiments comprising a switch module having a switch sleeve and a blocking sleeve it is preferable that the second engagement element also remains at the end of the dispensing stroke such that the second engagement element prevents the blocking sleeve from being moved in the distal direction relative to the housing and/or the second engagement element, whereby the switch sleeve and/or the needle protective sleeve are slideable in the distal direction relative to the blocking sleeve, in particular, by means of the energy stored in the second spring, causing the needle protective sleeve to be moved, in particular, into its needle protective position. As already described and noted only for the sake of completeness, the locking element between the blocking sleeve and the switch sleeve can be brought into an engagement that prevents the switch sleeve from being slideable in the proximal direction relative to the blocking sleeve. Preferably, a movement of the blocking sleeve in the proximal direction is prevented by the blocking sleeve striking either against the housing or against a stationary element such as, for example, a mechanism holder within the housing, or against the signal element.

Another aspect of the invention relates to the design of a product container, in particular, a tip holder for an autoinjector, in particular, for an autoinjector in which the product container is not slideable relative to the housing and/or for an autoinjector of the type described above.

The invention is based on a syringe module which is provided, in particular, for use in an autoinjector. In particular, an autoinjector having said syringe module can be provided. The syringe module comprises a syringe and a syringe holder. The syringe comprises a syringe body, a piston, and a needle, with the needle being, for example, non-detachably secured to a needle holding section of the syringe, and the piston being slideably arranged in a cylindrical section of the syringe body, with the syringe body having a tapering section or area arranged between the needle holding section and the cylindrical section. The syringe further comprises a needle protective cap, which can be, for example, a so-called soft needle shield or, preferably, a rigid needle shield. A soft needle shield is preferably constructed of rubber-elastic plastic, and a rigid needle shield is constructed of a rigid plastic sleeve in which a sleeve of a rubbery plastic is arranged. The sleeve made of rubbery plastic and the rigid plastic sleeve together form the rigid needle shield. The needle protective cap, which covers the needle and is fastened to the needle holding section, extending, in particular, to the needle holding section extending conically in the direction of the needle tip, preferably protects the needle from soiling and keeps it sterile. A gap is formed between the tapering section and the needle protective cap, in particular, the rigid plastic sleeve.

The syringe holder comprises at least one engagement element, in particular, a shoulder against which the tapering section of the syringe is supported in the distal direction and which engages in the gap between the needle protective cap and the tapering section. Advantageously, resting of the tapering section against the at least one shoulder prevents the syringe from being able to move in the distal direction relative to the syringe holder.

It is preferred for a gap to exist or form between the shoulder and the needle protective cap so as to prevent force from being exerted on the needle protective cap by the shoulder. This advantageously prevents the sterility of the needle from being compromised by an unintentional displacement of the needle protective cap by the shoulder.

In preferred embodiments, the syringe body may comprise a finger flange on its proximal end, whereby a gap is formed between the finger flange and the syringe body when the tapering section rests against the shoulder, causing essentially no force to be exerted on the finger flange. This advantageously prevents too much force from being exerted on the finger flange causing the syringe body to break.

It is further preferred for the syringe holder to comprise at least one holding element, in particular, a projection directed outward with which the syringe holder can be connected or is connected with a housing of the autoinjector in an axially fixed manner, in particular, is snapped on or capable of being snapped on.

In particular, the syringe holder may comprise at least one cam, which is elastically arranged, in particular, on an arm and is arranged, for example, distal to the holding element. The at least one cam can inhibit or prevent a needle protective sleeve from moving from its starting position into its actuated position such that when a limiting force is exceeded that is exerted on the needle protective sleeve along the longitudinal axis L of the autoinjector, the at least one cam is pressed out of the engagement with the needle protective sleeve, enabling the needle protective sleeve to be abruptly moveable into its actuated position relative to the housing.

The housing of the autoinjector can, for example, comprise a holding section that rests against the syringe holder, in particular, against an outer surface or an outer circumference of the syringe holder and prevents the at least one engagement element from moving transversely to the longitudinal axis in a direction opposite the longitudinal axis. In particular, the holding section can be ring-shaped and surround the at least one engagement element, preferably two or three or four engagement elements, so that the at least one engagement element is arranged within the holding section. During assembly and/or placement of the syringe in the syringe holder, the syringe holder is not engaged with the holding section of the housing. When the syringe is placed completely in the syringe holder, in particular, the at least one engagement element engages in the gap between the tapering section and the needle protective cap, the syringe module and/or the syringe holder is brought into engagement with the holding section, so that the at least one engagement element is prevented from moving out of engagement with the tapering section transverse to the longitudinal axis, in particular, in a direction opposite the longitudinal axis or outward.

In a first variant, the at least one engagement element may be formed elastically, in particular, on one arm on the syringe holder, whereby the syringe is pushed with its proximal end and with the needle facing forward into the syringe holder, which is preferably sleeve-shaped, whereby the needle protective cap deflects the at least one engagement element outward transverse to the longitudinal axis, i.e., in a direction opposite the longitudinal axis, whereby, if the needle protective cap was moved completely past the at least one engagement element, the at least one engagement element snaps into the gap between the tapering area and the needle protective cap. Subsequently, the syringe holder with the syringe is moved into engagement with the holding section of the housing of the autoinjector, allowing the at least one engagement element to be held in engagement with the gap between the needle protective cap and the tapering section and can no longer spring out of this engagement. In another variant, the syringe holder can comprise at least two shell bodies, in particular, two half-shells, preferably each comprising such an engagement element. The engagement element may be arranged rigidly, i.e., essentially immovably on the shell body. By joining together the at least two shell bodies, the at least one engagement element can be inserted into the gap between the needle protective cap and the tapering section of the syringe arranged between the shell bodies, which blocks the syringe from moving into the distal direction.

In particular, two shell bodies can be connected via a pivotable joint, allowing the shell bodies to be pivoted relative to one another from an insertion position, in which the syringe can be placed in the syringe container, into a closing position in which the at least one engagement element engages in the gap between the needle protective cap and the tapering area. The shell bodies can lock, or be locked, together in the closing position, or alternatively rest loosely against each other whereby the shell bodies are held together by the holding section.

Since the shell bodies are preferably formed of plastic, such as e.g. transparent plastic, the pivoting joint can be a film hinge, so that the first and second shell bodies are integrally connected by the film hinge.

Alternatively, the pivoting joint can be a hinge having at least one hinge pin and at least one hinge pin holder in which the hinge pin is arranged, in particular, is locked in place, and relative to which the hinge pin is pivotable and/or on along which the hinge pin slides during pivoting. For example, the first shell body can comprise two hinge pins and the second shell body can comprise two hinge pin holders for the two hinge pins. Preferably, the first shell body comprises one hinge pin and one hinge pin holder each, with the second shell body likewise comprising one hinge pin and one hinge pin holder each and the hinge pin of the one shell body is inserted, or can be inserted, into the hinge pin holder of the other shell body. The advantage hereby is that the first shell body and the second shell body can be formed in the same way and can be quickly joined together, so that the tooling costs for production can be reduced.

The pivoting axis of the pivoting joint can be parallel or transverse, in particular, vertical or tilted relative to the longitudinal axis of the syringe, in particular, relative to the injection needle of the syringe. If the pivoting axis is parallel to the longitudinal axis, it is preferable that the pivoting axis is arranged laterally relative to the syringe body. If the pivoting axis is arranged transversely to the longitudinal axis, it is preferred that the hinge and/or the pivoting axis is arranged on the proximal end of the syringe holder.

In preferred embodiments, the first and second shell body can be joined together by a linear movement transversely to the longitudinal axis, and that at least one engagement element moved during joining into the gaps between the needle protective cap and the tapering area of the syringe body, in particular, by the linear joining movement. The first and second shell bodies can be locked or snapped in place on opposite sides relative to the syringe diameter; alternatively, they can loosely rest against one another, whereby the holding section of the housing of the autoinjector can hold the shell bodies together.

Preferably, the first shell body and the second shell body are connected in a joining position, in which the syringe can be placed in the syringe body, connected by means of at least one, preferably by a plurality of predetermined breaking points, whereby the at least one predetermined breaking point is broken by pressing together the first and the second shell body against one another, which brings the first and second shell bodies into their locked position, in which the at least one engagement element engages in the gap between the needle protective cap and the tapering area. Prior to breakage of the at least one predetermined breaking point, the first and the second shell body can be integrally joined together, whereby a sleeve-shaped body is formed into which the syringe can be inserted through the proximal end of the body, in particular, with the needle or the needle protective cap facing forward.

It is generally preferred that the first shell body and the second shell body comprise the at least one projection for the connection with the housing and/or the cam to provide resistance when the needle protective sleeve is pushed back.

In further embodiments, the first shell body can comprise the at least one engagement element whereby a lateral opening through which the syringe can be inserted laterally into the first shell body, and with lateral insertion of the syringe into the syringe body the at least one engagement element is inserted into the gap between the needle protective cap and the tapering section. For example, the first shell body can comprise the at least one projection and/or the at least one cam.

Preferably, the syringe holder comprises a second, in particular, sleeve-shaped shell body into which the first shell body can be inserted together with the syringe and with a movement along the longitudinal axis, in particular, through the proximal end of the second shell body and preferably with the needle tip or the needle protective cap facing forward. In the embodiment with the second shell body, the second shell body can optionally comprise the at least one projection and/or the at least one cam.

Preferably, the second shell body can comprise a translation motion stop, against which rests a translation motion counter-stop of the first shell body, so that a displacement of the first shell body housed in the second shell body is prevented in the distal direction relative to the second shell body, i.e., in particular, when the first shell body is inserted into the second shell body. The holding section of the housing can be preferably designed in such a way that the at least one engagement element of the first shell body is held in engagement with the tapering area and preferably also rests against the area of the second shell body in which the translation motion stop is formed.

In further preferred embodiments, the syringe holder can comprise at least one first sleeve-shaped shell body, in particular, a sleeve-shaped basic body and at least one, preferably two, pivoting levers, with the pivoting lever being pivotably arranged about a pivoting axis on the first shell body by means of a hinge. The pivoting axis can preferably extend transversely to the longitudinal direction of the syringe, preferably on a skewed line relative to the longitudinal axis of the syringe. The engagement element can be arranged on the pivoting lever, and with several pivoting levers preferably on each of the several pivoting levers, in particular, the end of the pivoting lever opposite the pivotal axis. Preferably, the engagement element is arranged at a position distal to the pivoting joint. The pivoting joint can be a film hinge which connects the pivoting lever and the first sleeve-shaped shell body. Alternatively, the pivoting joint can be a hinge having at least one hinge pin and at least one hinge pin holder in which the hinge pin is arranged, preferably locked in place, and relative to which the hinge pin is pivotable and/or along which the hinge pin slides during pivoting. Preferably, the pivoting lever can comprise two hinge pins and the sleeve body can comprise two hinge pin holders for the hinge pins of the pivoting lever, or vice-versa. When several pivoting levers are present, several such pivoting pin holders can accordingly be present.

Preferably, the holding section of the housing can act in such a manner on the at least one pivoting lever, in particular, be resting against the at least one pivoting lever, such that the engagement element is held in engagement with the tapering area of the syringe body. When the syringe is inserted via the proximal end of the sleeve body with the needle and/or in particular, the needle protective cap facing forward, the at least one engagement element is pivoted outward, causing the needle protective cap to be moved past the at least one engagement element, so that the at least one engagement element can engage in the gap if the gap is in the position of the at least one engagement element relative to the longitudinal axis.

Preferably, the cam for the needle protective sleeve can be formed on the pivoting lever. In particular, the pivoting lever can be a two-arm pivoting lever, whereby the cam is formed on one arm that preferably protrudes in the proximal direction from the pivoting joint, and where on the other arm that preferably protrudes in the distal direction from the pivoting joint, the at least one engagement element is formed. When the holding section of the housing holds the pivoting lever in engagement with the tapering area, the pivoting arm on which the cam is arranged can be elastically deformed when the needle protective sleeve is pushed back.

BRIEF DESCRIPTION OF THE DRAWINGS

FIG. 1 is an exploded representation of an autoinjector according to an especially preferred embodiment.

FIGS. 2a-2c are the autoinjector of FIG. 1 in a delivery state, in which FIGS. 2a to 2c are sectional views across the longitudinal axis of the device, whereby the sectional views are at different angles about the longitudinal axis.

FIGS. 3a-3c are the device and the views from FIGS. 2a-2c, whereby a needle protective sleeve is in its actuated position.

FIGS. 4a-4c are the device and the views from FIGS. 2a-2c, whereby the drive member is shown at the end of a first partial stroke of its dispensing stroke.

FIGS. 5a-5c are the device and the views from FIGS. 2a-2c, whereby a drive member is shown at the end of its dispensing stroke.

FIGS. 6a-6c are the device and the views from FIGS. 2a-2c, whereby a signal which signals the end of the dispensing of the product is generated.

FIGS. 7a-7c are the device and the views from FIGS. 2a-2c, whereby the needle protective sleeve is in its needle protective position.

FIGS. 10a-10d are perspective views of a syringe holder according to a third variant.

FIGS. 11a-11c are perspective views of a syringe holder according to a fourth variant.

FIGS. 8e, 9d, 10e, 11d, and 12d are longitudinal sections of the five embodiments in the delivery state and for the embodiments two to five, in a position with a partially and a completely inserted syringe, respectively.

DETAILED DESCRIPTION

Figure 8A:
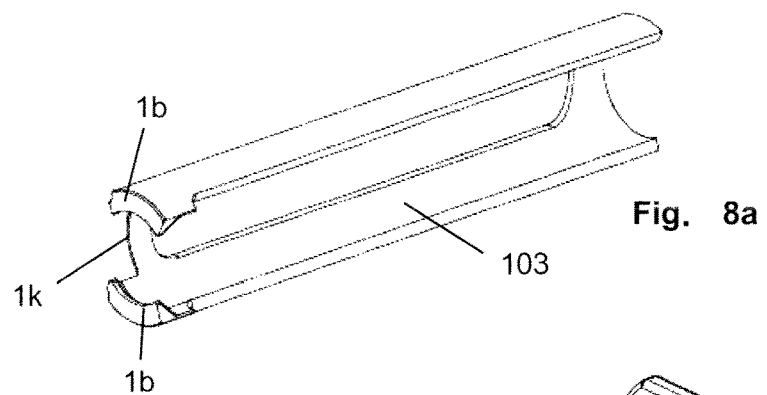
FIGS. 8a-8d are perspective views of a multipart syringe holder according to a first variant.
Figure 8B:
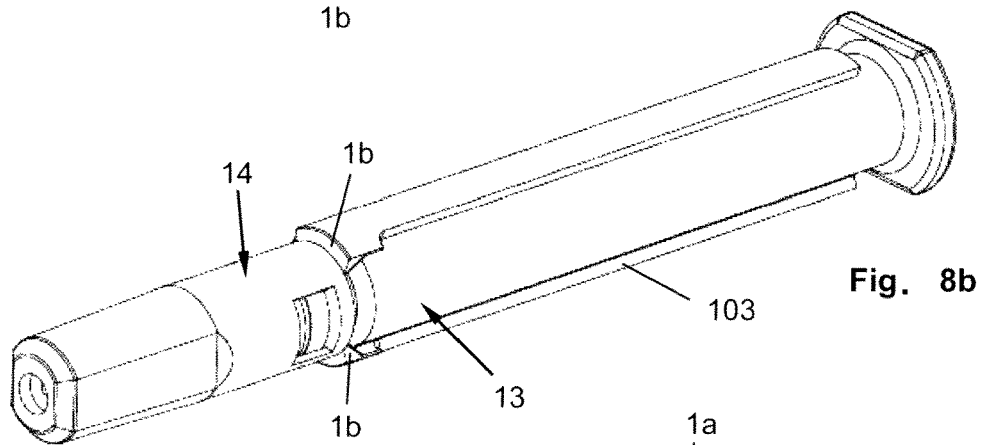
Figure 8C:
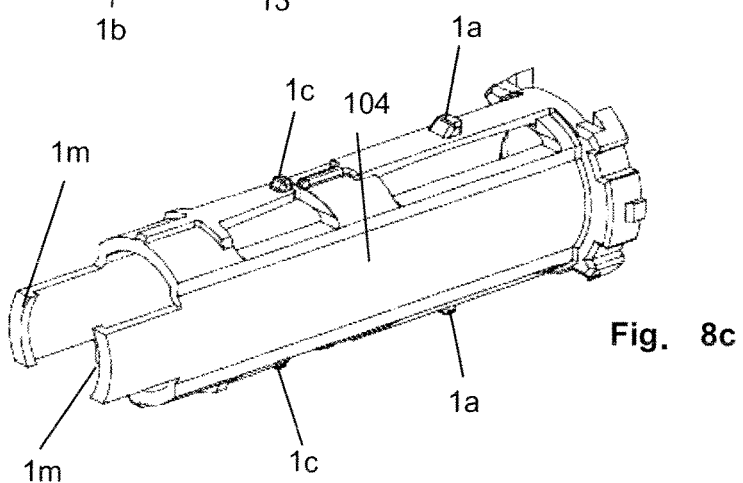

With reference to FIGS. 1-7c, the structural features and the function of the preferred autoinjector will now be described.

The autoinjector comprises a sleeve-shaped, longitudinal housing 2 with a longitudinal axis L, having a locking cap 12 on its proximal end, which is form-fittingly connected with the housing 2 for conjoint and axial rotation and forms the proximal end of the autoinjector. The locking cap 12 is snapped on the housing 2. To this end, the locking cap 12 comprises a locking element 12a, which is locked into a recess 2a on the housing 2, preferably in such a manner that the locking cap 12 cannot, or cannot be readily decoupled from the housing 2.

A pull cap 4 is arranged on the distal end of the autoinjector in its delivery state (FIGS. 2a-2c) that it is pulled off, or rotated off, and removed before the autoinjector is used.

A product container 13 in the form of a syringe is non-slidably accommodated in the housing 2—except when the autoinjector is assembled—along the longitudinal axis L relative to the housing 2. The product container 13 comprises a sleeve-shaped syringe body surrounding a piston 13*b* which sealingly rests against the inner circumference of the syringe body. On its distal end, the syringe body comprises an injection needle 13*a* that is, in particular, nondetachably connected to the syringe body, the distal end of which is formed by the needle tip. A liquid product, in particular, a medication, is located within the syringe body between the injection needle 13*a* and the piston 13*b*, whereby the liquid product is dispensed through the hollow injection needle 13*a* from the product container 13 by movement of the piston 13*b* in a dispensing direction, i.e., in the distal direction or toward the injection needle 13*a*. The syringe body comprises a so-called finger flange on its proximal end that projects radially outward beyond the outer circumference of the cylindrical syringe body.

The product container 13 is accommodated in a product container holder, which is referred to as a syringe holder 1, in such a way that it is secured against a movement at least along the longitudinal axis L in distal direction relative to the syringe holder 1. As can best be seen in FIG. 2*a*, the syringe holder 1 is connected with the housing 2 in a form-locking manner, in particular, it is locked in place. To this end, the housing 2 comprises recesses into which locking elements engage, which are formed on the proximal end of the syringe holder 1. The syringe holder 1 comprises at least one inward projected shoulder 1*b*, on which a tapering section of the product container 13 is supported which is distal to the cylindrical syringe body section that guides the piston 13*b*.

In order to prevent that the product container 13 is slideable in the proximal direction relative to the syringe holder 1, the proximal end of the product container 13 is pressed into engagement with the shoulder 1*b* by a holder acting on the syringe body. The holder is formed by a holder spring section 5*c* of a mechanism holder 5. The mechanism holder 5 is arranged in particular, non-slideable and/or for conjoint rotation relative to the housing 2 along the longitudinal axis L. The sleeve-shaped mechanism holder 5 can be snapped on the housing 2. By means of the holding spring section 5*c*, longitudinal differences of the product holder 13, which may arise as a result of manufacturing tolerances, can be compensated for, ensuring a fixed fitting of the product holder 13 on the shoulder 1*b*.

The product container 13 is arranged relative to the housing 2 such that the needle tip projects distally beyond the distal end of the housing 2. In the starting- or delivering position of the autoinjector, i.e., when the pull cap 4 is arranged on the autoinjector, the needle 13*a* is covered by a needle cover cap 14, which is designed in the example shown as a so-called rigid needle shield known to experts, or alternatively, as a soft needle shield in order to protect the needle 13*a* from soiling and/or to keep the needle 13*a* and the medication sterile. The rigid needle shield 14 is arranged on a needle holding section of the syringe body, whereby the tapering section of the syringe body is located between the needle holding section and the cylindrical section of the syringe body. The shoulder 1*b* is arranged between the syringe body and the proximal end of the rigid needle shield 14, in particular, such that between the rigid needle shield 14 and the shoulder 1*b*, a gap—while smaller—is formed in order to prevent the shoulder 1*b* from exerting a force on the rigid needle shield 14, that could, for example, compromise the sterility of the needle 13*a* or of the liquid product. The pull cap 4 is removably latched into the housing 2 or into a needle protective sleeve 3, whereby said latch is released when the pull cap 4 is removed from the housing 2 or the needle protective sleeve 3. The latch is formed in the example shown by a latch configuration 3*b* of the needle protective sleeve 3 and latch hook 4*a* of the pull cap 4 (FIG. 2*b*). These latch hooks 4*a* further secure the pull cap 4 against a proximal movement relative to the housing 2 by being fixedly supported on the housing 2 or on a distal front side on the syringe holder 1. The pull cap 4 also comprises in particular, a latch hook 4*a* with at least one snap 4*b* which engages in a gap between the syringe body, in particular, in its tapering area, and the proximal end of the rigid needle shield 14. When the pull cap 4 is removed from the autoinjector, the snap 4*b* latches into the proximal end of the rigid needle shield 14, whereby the rigid needle shield 14 becomes detached from the product holder 13 and is removed together with the cover cap 4 from the autoinjector.

The autoinjector comprises a needle protective sleeve 3 which can be displaced relative to the housing 2 and along the longitudinal axis L by an activation stroke $H_B$ in the proximal direction into an actuated position in order to trigger the dispensing of the product. In the starting position of the needle protective sleeve 3, as it is shown in FIGS. 2*a*-2*c*, where the pull cap 4 is removed, the distal end of the needle protective sleeve 3 protrudes distally over the needle tip of the needle 13*a*, so that access to the needle tip is initially prevented. By displacing the needle protective sleeve 3 by the activation stroke $H_B$, the needle protective sleeve 3 is moved in such a distance in proximal direction so that the needle 13*a* projects from the distal end of the needle protective sleeve 3, in particular, with a length corresponding to the injection depth of the needle into the injection site. Preferably, the needle 13*a* should project beyond the distal end of the needle protective sleeve 3 to such an extent that a subcutaneous injection can be carried out. In particular, the housing 2 can form a stop 2*c* against which the needle protective sleeve 3 comes to rest when it is in the actuated position.

After the completed injection, the needle protective sleeve 3 can be moved relative to the housing 2 along the longitudinal axis L by a needle protective stroke $H_N$ in the distal direction from the actuated position and into a needle protective position (FIGS. 7*a*-7*c*). In the needle protective position, the distal end of the needle protective sleeve 3 projects distally beyond the needle tip, so that access to the needle tip is prevented and risk of injury risk is reduced. As describer further below, the needle protective sleeve 3 can be blocked against a renewed pushing back from the needle protective position.

The syringe holder 1 has a projection 1*a* pointing radially outward whereby the projection 1*a* engages in a slit-shaped recess of the needle protective sleeve 3 located between the housing 2 and the syringe holder 1. In the starting position of the needle protective sleeve 3 (FIGS. 2*a*-2*c*) and/or in the needle protective position of the needle protective sleeve 3 (FIGS. 7*a*-7*c*), the needle protective sleeve 3, in particular, the proximal end of the slit-shaped recess, rests against the projection 1*a* thereby preventing movement of the needle protective sleeve 3 in the distal direction. Into this slit-shaped recess, alternatively into another recess of the needle protective sleeve 3, a cam 1*c* which is elastically arranged on the syringe holder 1 and formed by the syringe holder 1 may engage. The cam 1*c* is designed in such a way that with an attempt at moving the needle protective sleeve 3 from the starting position into the actuated position, the cam 1*c* initially prevents the movement of the needle protective sleeve 3, whereby the cam 1*c* is pressed out when the force applied to the needle protective sleeve 3 for pushing back exceeds a certain threshold value, causing the needle protective sleeve 3 to be abruptly pushed back into the actuated position. In this way, the needle 13*a* can be abruptly inserted into the injection site. For inserting the needle 13*a* and/or for displacing the needle protective sleeve 3 into the actuated position, the distal end of the needle protective sleeve 3 is placed on the injection site, whereby the housing 2 is then pressed in the direction of the injection site; if the pressing force exceeds the aforementioned threshold value, the housing 2 is abruptly moved toward the puncture site and the needle protective sleeve 3 into the actuated position relative to the housing 2.

The housing 2 comprises a ring-shaped holding section or a ring section 2*b* which, in particular, circularly surrounds the distal end of the syringe holder 1 and rests against it, causing the at least one shoulder 1*b* to be held in engagement with the tapering area of the syringe body. The housing 2 further comprises a translation motion stop in form of a holding shoulder 2*e* in the area of the holding section 2*b* that prevents the syringe holder 1 from being slideable in the distal direction relative to the housing 2 when the syringe holder 1 rests against the holding shoulder 2*e*. This also advantageously applies for the variants described.

The autoinjector also comprises a sleeve-shaped drive member 7 which forms a shoulder projecting inward on its distal end, on which a first spring 9 is supported, which can also be referred to as dispensing spring. The first spring 9 is arranged within the sleeve-shaped drive member 7. The first spring 9 is a coiled spring acting as a compression spring, which is pretensioned in the starting- or delivery position of the autoinjector with so much energy that it can dispense the product contained in the product container 13, in particular, completely out of the product container 13 by movement of the drive member 7 by one dispensing stroke $H_A$. In the delivery state of the device, there is a space between the piston 13*b* and the distal end of the drive member 7, so that the drive member 7 strikes the piston 13*b* and transports it along in the dispensing direction only while the dispensing stroke $H_A$ is being executed.

The first spring 9 is supported with its proximal end on a holding element 6 comprising in this example two arms 6*c*, whereby on each arm 6*c* a first engagement element 6*a* and a second engagement element 6*b* is arranged. The first engagement element 6*a* points radially toward the longitudinal axis L, and the second engagement element 6*b* points radially away from the longitudinal axis L. The first engagement element 6*a* engages in a first recess 7*a* which is formed by the drive element 7 thereby preventing the movement of the drive member 7 in the distal direction or in the dispensing direction relative to the holding element 6. In this way, the first spring 9 is held in its tensioned state. The holding element 6 comprises a guide pin 6*d* which is inserted through the proximal end of the first spring 9 into the core of spring 9. The guide pin 6*d* prevents lateral outward bending of the first spring during and at the end of the dispensing stroke $H_A$ of the drive member 7.

The autoinjector comprises a switch module 8, 15 having a switch sleeve 15 and a blocking sleeve 8 surrounded by the switch sleeve 15. In the delivery state of the device, the first engagement element 6*a* is held in the engagement with the first recess 7*a* by the inner circumference of the blocking sleeve 8 that rests against the second engagement element 6*b*.

The switch sleeve 15 is connected with the proximal end 3*a* of the needle protective sleeve 3 or at least rests against the proximal end 3*a* of the needle protective sleeve 3. A second spring 10 within which the first spring 9 is located and which preferably at least partially surrounds the switch sleeve 15 and the blocking sleeve 8 is supported with its distal end on the switch sleeve 15. A part of the switch sleeve 15 is thus situated between the needle protective sleeve 3 and the distal end of the second spring 10. The second spring 10 is a metal spring acting as a compression spring and designed as a coiled spring. The proximal end of the second spring 10 is supported on a signal element 11, in particular, on a projection 11*c* that is axially displaceable and engages or conjoins with the housing 2 and which reaches through a slit-shaped groove 5*b* of the mechanism holder 5. The second spring 10 thus also surrounds the mechanism holder 5 at least partially, preferably completely.

The switch element 15 comprises a recess 15*a* in which a locking element 8*a* of the blocking sleeve 8 engages. The locking element 8*a* is sawtooth-shaped and protrudes radially away from the longitudinal axis L. The locking element 8*a* is elastically arranged on one arm formed by the blocking sleeve 8. By movement of the switch sleeve 15 in proximal direction, the blocking sleeve 8 is transported in proximal direction via the engagement of the locking element 8*a*.

By movement of the needle protective sleeve 3 into the actuated position, the switch sleeve 15 is likewise transported by the activation stroke $H_B$, whereby the second spring 10 is tensioned. If the needle protective sleeve 3 is not completely moved into the actuated position, the second spring 10 can move the switch sleeve 15 and the needle protective sleeve 3 back into the starting position, whereby the blocking sleeve 8 is also transported by the switch sleeve 15 via engagement with the locking element 8*a*.

In the delivery state or, prior to triggering of product dispensing, the sleeve-shaped signal element 11 is in an axially fixed engagement with the drive member 7. The signal element 11 comprises a first engagement element 11*a*, which engages in a recess 7*b* of the drive member 7, and a second engagement element 11*b*. The first engagement element 11*a* and the second engagement element 11*b* are elastically arranged on the end of one arm 11*d*. The signal element 11 comprises two such arms 11*d* with a first engagement element 11*a* and a second engagement element 11*b*. The first engagement element 11*a* points radially toward the longitudinal axis L and the second engagement element 11*b* points radially away from the longitudinal axis L. In the delivery state, the first engagement element 11*a* is held by the inner circumference of the blocking sleeve 8 in axially fixed engagement with the drive member 7. The second engagement element 11*b* rests against the inner circumference of the blocking sleeve 8. The locking cap 12 comprises a signal stop 12*b*, against which the signal element 11 can strike to generate a signal and preferably rests against the signal element 11 in the delivery state of the device.

To administer the product from the product container 13, the pull cap 4 is removed from the autoinjector together with the rigid needle shield 14. The distal end of the needle protective sleeve 3 is placed on the injection site of a patient, whereby the housing 2 is displaced toward the injection site, causing the needle protective sleeve 3 to be moved by the activation stroke $H_B$ from its starting position into the actuated position in the proximal direction relative to the housing 2. In this way, the second spring 10 is tensioned, whereby the switch sleeve 15 is transported along by the needle protective sleeve 3 by the activation stroke $H_B$. The blocking sleeve 8 comprises a first recess 8*b* which, as shown in FIGS. 3*a*-3*c*, is brought to the position of the second engagement element 6*b* of the holding element 6 by movement of the blocking sleeve 8 by the activation stroke $H_B$ along the longitudinal axis L. In this way, the first engagement element 6a is moved out of engagement with the drive member 7 with a movement transverse to and away from the longitudinal axis L, whereby simultaneously the second engagement element 6b is moved into engagement with the blocking sleeve 8, especially with its first recess 8b. This releases the drive member 7 for movement in the dispensing direction by the dispensing stroke $H_A$.

Since the axially fixed coupling between the drive member 7 and the holding element 6 is now released, the holding element 6, which is moveable by least some distance relative to the housing 2 and along the longitudinal axis L, can be moved by the first spring 9 in the proximal direction, whereby the holding element 6 transports the blocking sleeve 8 by a start signal stroke $H_K$ (FIG. 3c) via engagement of the second engagement element 6b in the recess 8b, causing the blocking sleeve 8 to strike against a start signal stop 5a, which is formed by the mechanism holder 5, and thereby emits an acoustic and/or tactile signal which signals the user of the device that dispensing of the product has started. The movement of the blocking sleeve 8 by the activation stroke $H_B$, releases the locking element 8a for a movement transversely to and toward the longitudinal axis L, since the mechanism holder 5 comprises an indentation 5d which allows such movement of the locking element 8a when the blocking sleeve 8 was moved by the activation $H_B$, or when the needle protective sleeve 3 is in its actuated position.

Since the signal element 11 is still axially fixedly connected with the drive member 7, it is transported in the dispensing direction by a first partial stroke $H_S$ of the dispensing stroke $H_A$, whereby the signal element 11 is moved by approximately the first partial stroke $H_S$ away from the signal stop, as can best be seen in FIG. 4c. At the end of the first partial stroke $H_S$, during which the first and second engagement elements 11a, 11b are moved relative to the blocking sleeve 8, the first engagement element 11a is pressed out of its engagement with the drive member 7, whereby the second engagement element 11b is simultaneously moved into the second recess 8c of the blocking sleeve 8 in a movement transverse to the longitudinal axis L and radially away from the longitudinal axis L. This prevents the signal element 11 from moving in the proximal direction relative to the housing 2 or the blocking sleeve 8. The second engagement element 11b is held by the outer circumference of the drive member 7 in engagement with the recess 8c (FIG. 4a), when the drive member 7 is moved by its second partial stroke of the dispensing stroke $H_A$. The outer circumferential surface of the drive member 7 holds the second engagement element 6b in engagement with the first recess 8b of the blocking sleeve 8, as can best be seen in FIG. 4b. At the end of the dispensing stroke $H_A$, the drive member 7 releases the second engagement element 11b from engagement with the blocking sleeve 8, causing the second engagement element 11b to be moved out of engagement with the recess 8c, in particular, toward the longitudinal axis L, so that the second spring 10 accelerates the signal element 11 against the dispensing direction, i.e. in the proximal direction, so that when the signal element 11 strikes the signal stop 12b, an acoustic and/or tactile signal is generated.

As can best be seen in FIG. 5b, the engagement of the second engagement element 6b in the first recess 8b remains, which prevents a movement of the blocking sleeve 8 in the distal direction relative to the housing 2.

By removing the autoinjector from the injection site, the second spring 10 can move the switch sleeve 15 and the needle protective sleeve 3 from the actuated position into the needle protective position by the needle protective stroke $H_N$, whereby the locking element 8a is pressed out of the engagement with the recess 15a, and the switch sleeve 15 is moved in the distal direction relative to the blocking sleeve 8. If the needle protective sleeve 3 is in its needle protective position, the locking element 8a snaps on the switch sleeve 15, whereby the locking element 8a prevents the needle protective sleeve 3 from being pushed back into its actuated position. In the attempt to push back the needle protective sleeve 3 from the needle protective position into the actuated position, the switch element 15 strikes the locking element 8a, which prevents the movement of the needle protective sleeve 3 into the actuated position. To this end, the blocking sleeve 8 is supported axially on the start signal stop 5a of the mechanism holder 5.

Various embodiments of a syringe holder are shown in the following that can be used with an autoinjector, preferably, however, not necessarily an autoinjector of the type described above.

The syringe module of FIGS. 8a to 8d comprises a first shell body or sleeve body 103 which has a lateral opening and at least one, i.e., in the example shown, two shoulder-shaped engagement elements 1b, which project inwards, i.e., toward the longitudinal axis of the sleeve body 103.

The sleeve body 103 further comprises a translation motion counter-stop 1k pointing in the distal direction. For the assembling of the syringe 13 (FIG. 8b), it is inserted laterally into the sleeve body 103, i.e., with a movement transverse to the longitudinal axis, whereby the at least one engagement element 1b is inserted into the gap between the needle protective cap 14 and the tapering section of the syringe body of the syringe 13.

The syringe module further comprises a second shell body, in particular, sleeve body 104 (FIG. 8c) that is open on its proximal end and on its distal end comprises at least one, i.e., in the example shown two translation motion stops 1m projecting radially inwards. Like the syringe holder 1 in the embodiment in FIGS. 1 to 7c, the sleeve body 104 comprises at least one cam 1c, namely two cams 1c and at least one projection 1a, namely two projections 1a. The cam 1c is arranged elastically on the sleeve body 104 via an arm.

Figure 8D:
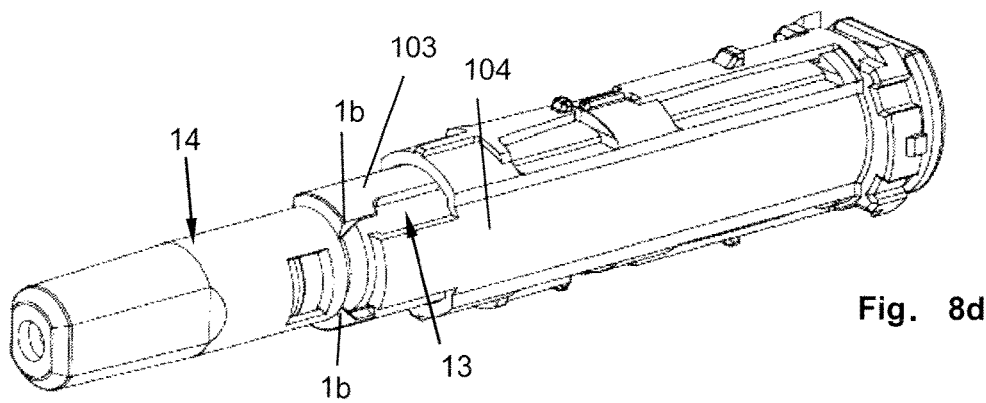

The unit consisting of the syringe 13, the needle protective cap 14, and the first sleeve body 103 is inserted into the second sleeve body 104 (FIG. 8c) via the proximal end along the longitudinal axis with the needle protective cap 14 pointing forward (FIG. 8b), whereby the translation motion counter-stop 1k strikes the translation motion stop 1m, when the unit 13, 14, 103 has been completely inserted into the sleeve body 104 (FIG. 8d). The unit shown in FIG. 8d is then moved in the housing 2 of the autoinjector in such a way during assembly that the holding section 2b, in particular, the circular holding section or ring section rests against the at least first sleeve body 103, at least against the area of the engagement element 1b, so that the engagement element 1b is held in engagement with the tapering section of the syringe body. The holding section 2b can further also rest against the second sleeve body 104, in particular, in the area on which the at least one translation motion stop 1m is formed, in order to keep the translation motion stop 1m in engagement with the translation motion counter-stop 1k.

Figure 9A:
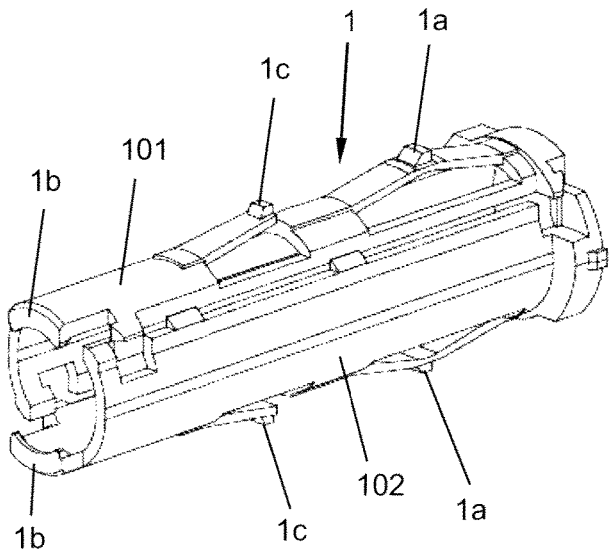
FIGS. 9a-9c are perspective views of a syringe holder according to a second variant.
Figure 9B:
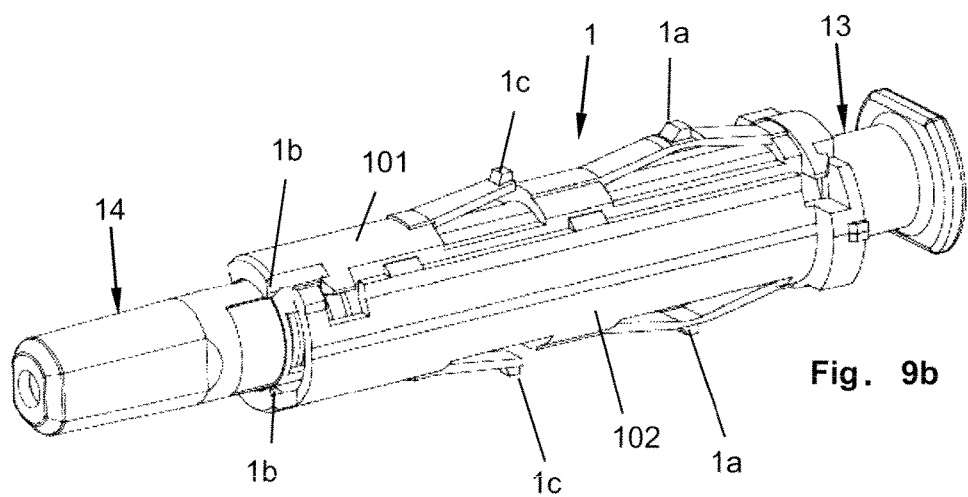
Figure 9C:
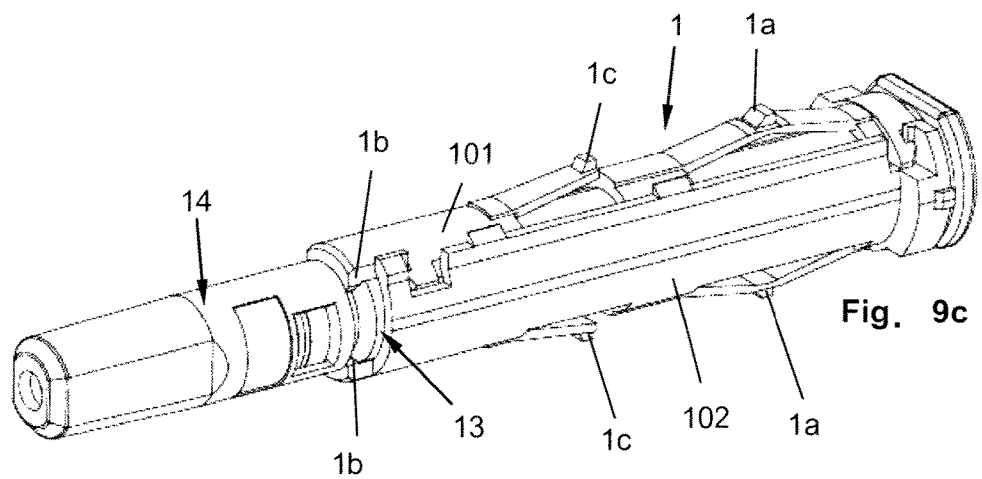
Figure 10E:
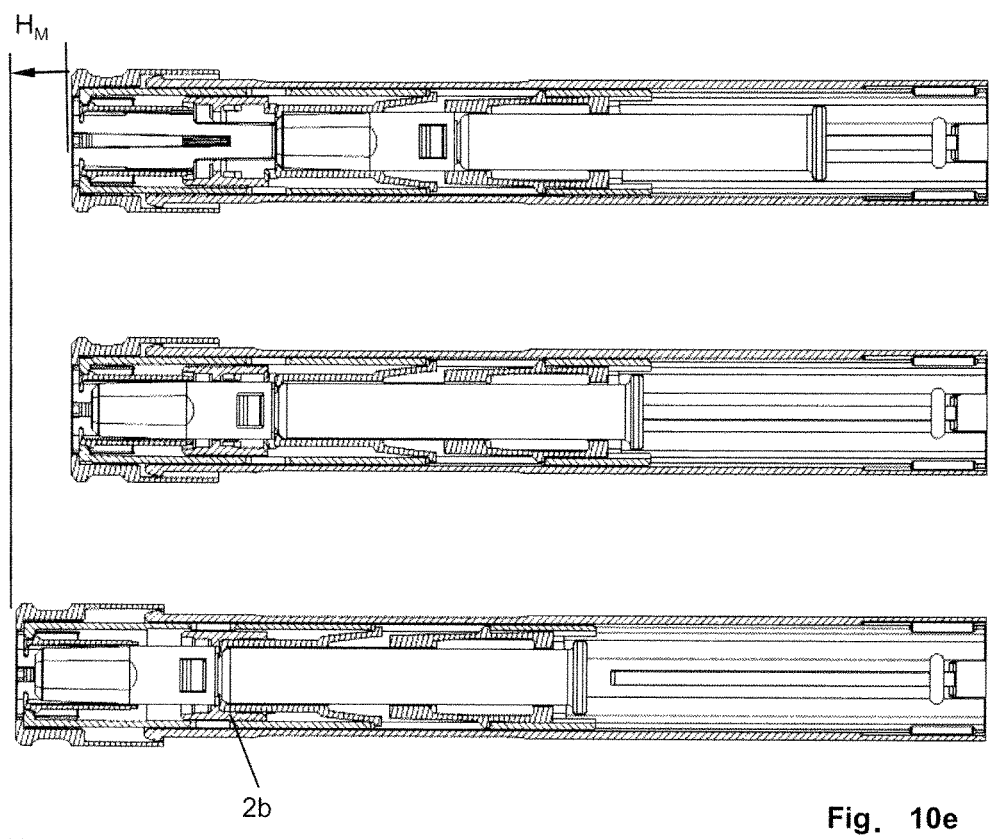

In the embodiment shown in FIGS. 9a-9c, the syringe module, in particular, the syringe holder 1, comprises a first shell body 101 and a second shell body 102, each formed as half-shells.

Each shell body 101, 102 comprises a cam 1c and a projection 1a in the manner described herein.

In the view shown in FIG. 9a, the first shell body 101 and the second shell body 102 are integrally connected with one another via several predetermined breaking points, whereby the first and second shell body 101, 102 assume an insertion position relative to one another. The syringe 13 is inserted in the distal direction with the needle protective cap 14 pointing forward (FIG. 9b) through the proximal end of the bodies 101, 102, shown in FIG. 9a, until the gap between the tapering section and the needle protective cap 14 along the longitudinal axis L is in the same position as the at least one engagement element 1b. In the example shown, each of the first and second shell body 101, 102 comprises an engagement element 1b. By pressing the first and second shell body 101, 102 against one another transverse to the longitudinal axis L the predetermined breaking points are broken, causing the first and second shell body 101, 102 to lock together in a form-locking manner, and the engagement elements 1b to move into the gap. As already described, the areas of the first and second shell body 101, 102, on which the engagement element 1b is formed, can be surrounded by the holding section 2b of the housing 2, whereby the engagement elements 1b are held in the engagement with the tapering area of the syringe body. With particular preference, during the insertion of the syringe 13 transverse to the longitudinal axis, the shell bodies 101, 102 can move into the insertion position against the elastic force of the arms which carry the projection 1a and/or the cam 1c. As described, here too the engagement elements 1b can likewise be subsequently brought and held in engagement by the holding section 2b of the housing 2 with the tapering section of the syringe body 13. Alternatively or additionally, the first shell body 101 and the second shell body 102 can be locked together in the closing position (FIG. 9c) in which the engagement elements 1b engage in the gap.

In the embodiment shown in FIGS. 10a-10d, the syringe holder 1 comprises a first shell body 101 and a second shell body 102, each formed as a half-shell and, in particular, are of an identical design, so that tooling costs can be reduced.

Each first and second shell body 101, 102 comprises a cam 1c and a projection 1a in the manner described. Further, each of the first and second shell body 101, 102 comprises an engagement element 1b on its distal end.

Each of the shell body 101, 102 comprises a hinge pin 1e and a hinge pin holder 1f (FIG. 10a), wherein the hinge pin 1e of the one shell body 101, 102 is inserted into the hinge pin holder 1f of the other shell body 102, 101 (FIG. 10b), so that the first and second half-shell 101, 102 can pivot relative to one another about the pivoting axis of the pivoting joint 1e, 1f, which is formed by the hinge pin 1e and the hinge pin holder 1f, namely between an insertion position (FIG. 10c) and a closing position (FIG. 10d). The syringe 13 is inserted together with the needle protective cap 14 through the proximal end of the syringe body 1, with the needle protective cap 14 being moved past the engagement element 1b, whereby the first shell body 101 and the second shell body 102 are pivoted relative to one another when the gap between the needle protective cap 14 and the tapering area of the syringe body is in the same position as the engagement elements 1b relative to the longitudinal axis L. This causes the engagement elements 1b to engage in the aforementioned gap. As described, the engagement elements 1b can be held in engagement with the tapering section of the syringe body by the holding section 2b of the housing 2. Alternatively, or additionally, the first shell body 101 and the second shell body 102 can lock together in the closing position (FIG. 10d) in which the engagement elements 1b engage in the gap.

Figure 11D:
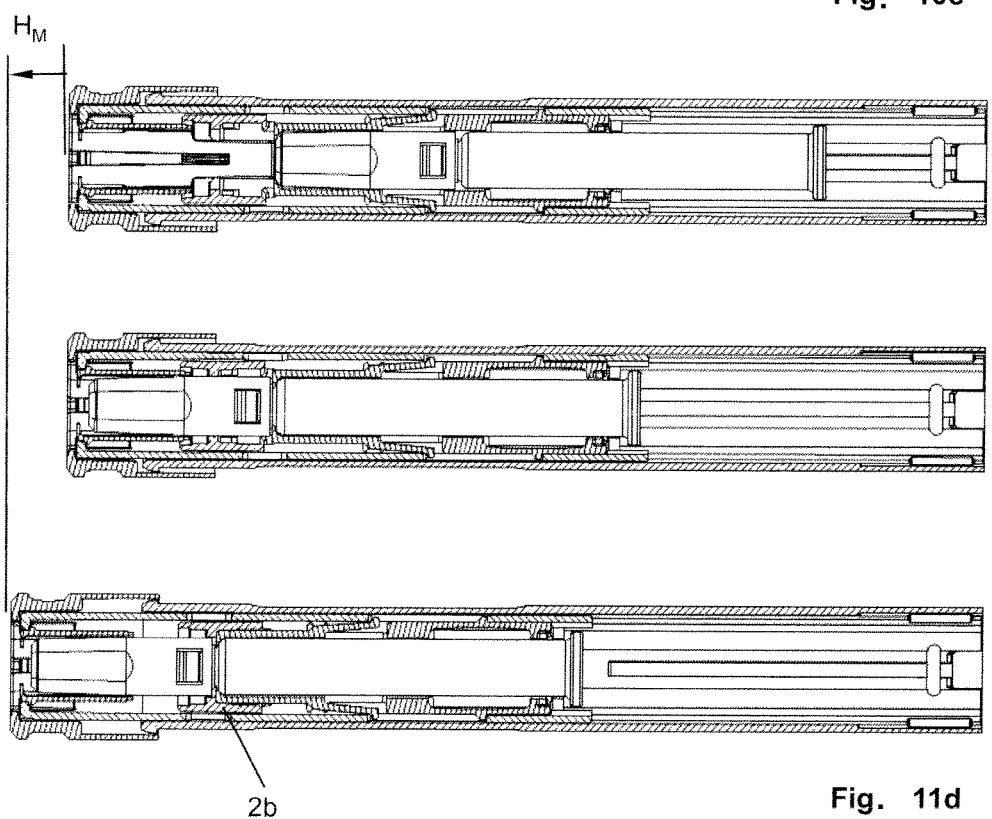

FIGS. 11a to 11c show an embodiment of the syringe holder 1 which has a first sleeve body 103 and two pivoting arms 1h. The projection 1a is formed on the sleeve body 103. The sleeve body 103 forms two hinge pin holders 1g for each of the pivoting arms 1h, in which one hinge pin 1i of the pivoting lever 1h is each arranged. Each of the pivoting levers 1h forms two hinge pins 1i which are locked together with the hinge pin holder. The pivoting pin 1i can be rotated relative to the pivoting pin holder 1g and can slide along the hinge pin holder 1g. The pivoting lever 1h comprises a lever section pointing in distal direction, whereby on the distal end of this lever section the engagement element 1b formed by the pivoting lever 1h, is formed for engagement in the gap between the needle protective cap 14 and the tapering section of the syringe body.

The pivoting lever 1h shown in the example has two arms, whereby the lever section protruding from the pivoting joint 1g, 1i in the opposite direction as the arm that forms the engagement element 1b, forms the cam 1c.

The syringe 13 is introduced with the needle protective cap 14 pointing forward through the proximal end of the sleeve body 103 into the sleeve body 103 with the needle protective cap 14 being moved past the engagement elements 1b until the gap between the tapering area of the syringe body and the needle cap 14 is in the same position relative to the longitudinal axis as the engagement elements 1b. By pivoting the pivoting lever 1h, the engagement elements 1b are pivoted into the gap and/or toward the longitudinal axis. The unit shown in FIG. 11c is then arranged in the housing 2 of the autoinjector in such a way that the holding section 2b fixes the pivoting lever 1h such that the engagement elements 1b are held in engagement with the tapering section of the syringe body. The arm on which the cam 1c is formed can be elastically deformed relative to the arm on which the engagement element 1b is formed, allowing the cam 1c to fulfill the intended function in terms of the needle protective sleeve 3. In particular, the cam 1a serves as a stop for the needle protective sleeve 3, whereby the needle protective sleeve 3 rests against the cam 1a when the needle protective sleeve is in its starting position and/or in its needle protective position.

In the fifth embodiment shown in FIGS. 12a-12d, the syringe module, in particular, the syringe holder 1, comprises a sleeve body 103. The sleeve body 103 comprises in particular, two cams 1c and, in particular, two projections 1a in the manner shown herein.

Figure 12A:
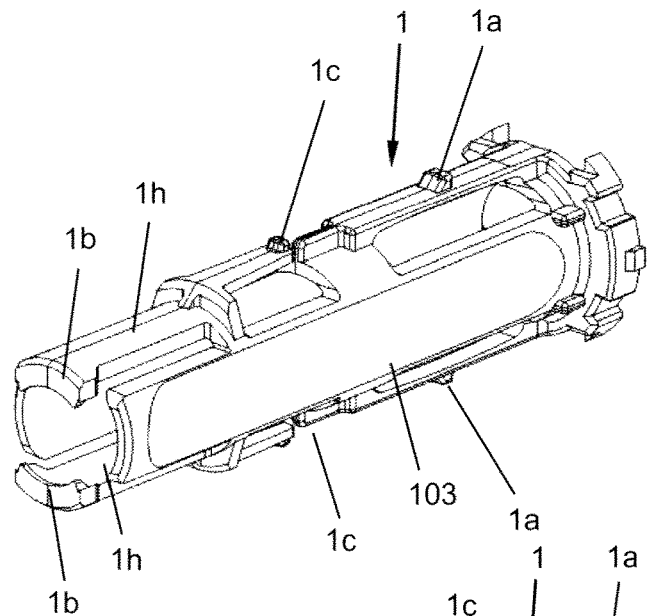
FIGS. 12a-12c are perspective views of a syringe holder according to a fifth variant.
Figure 12B:
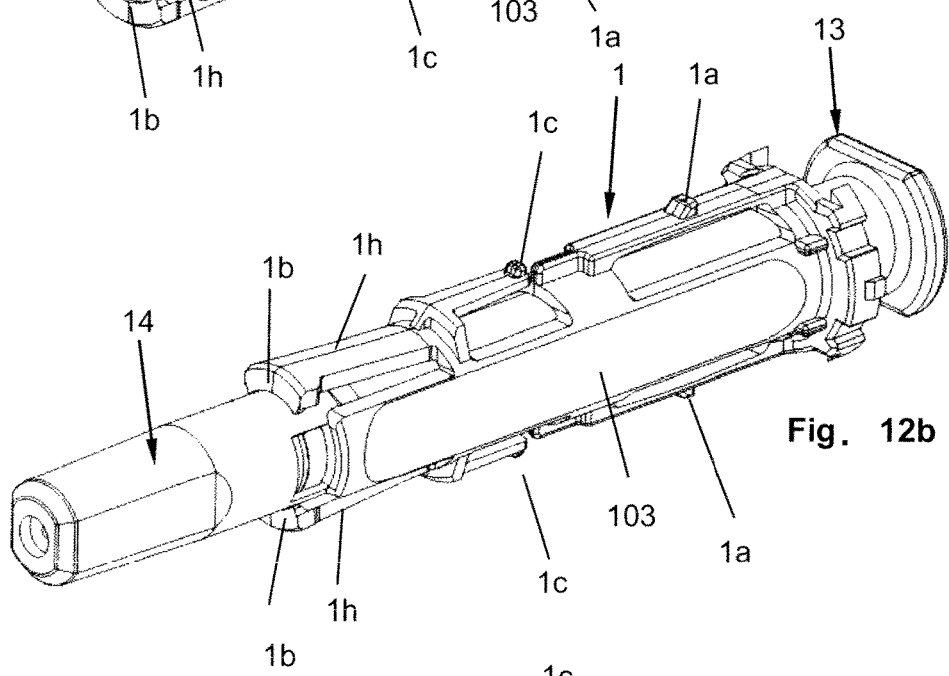
Figure 12C:
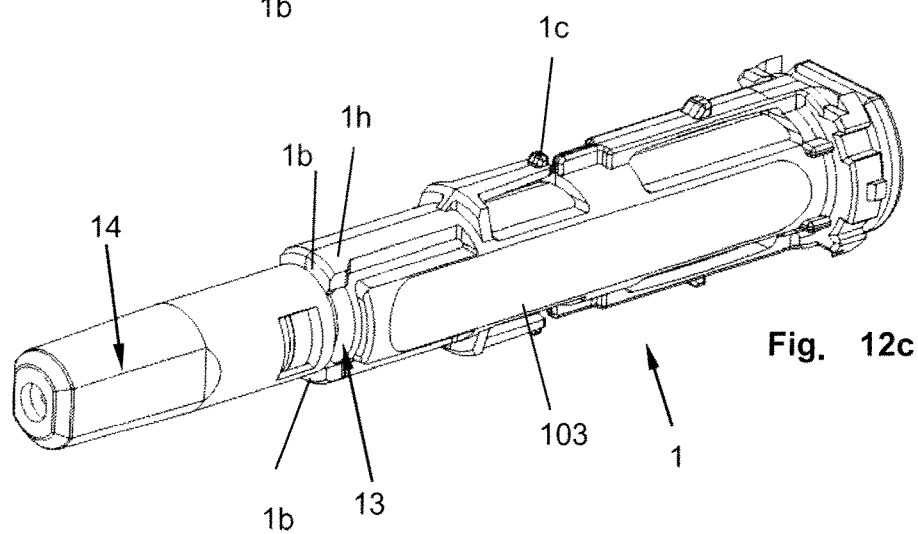
Figure 12D:
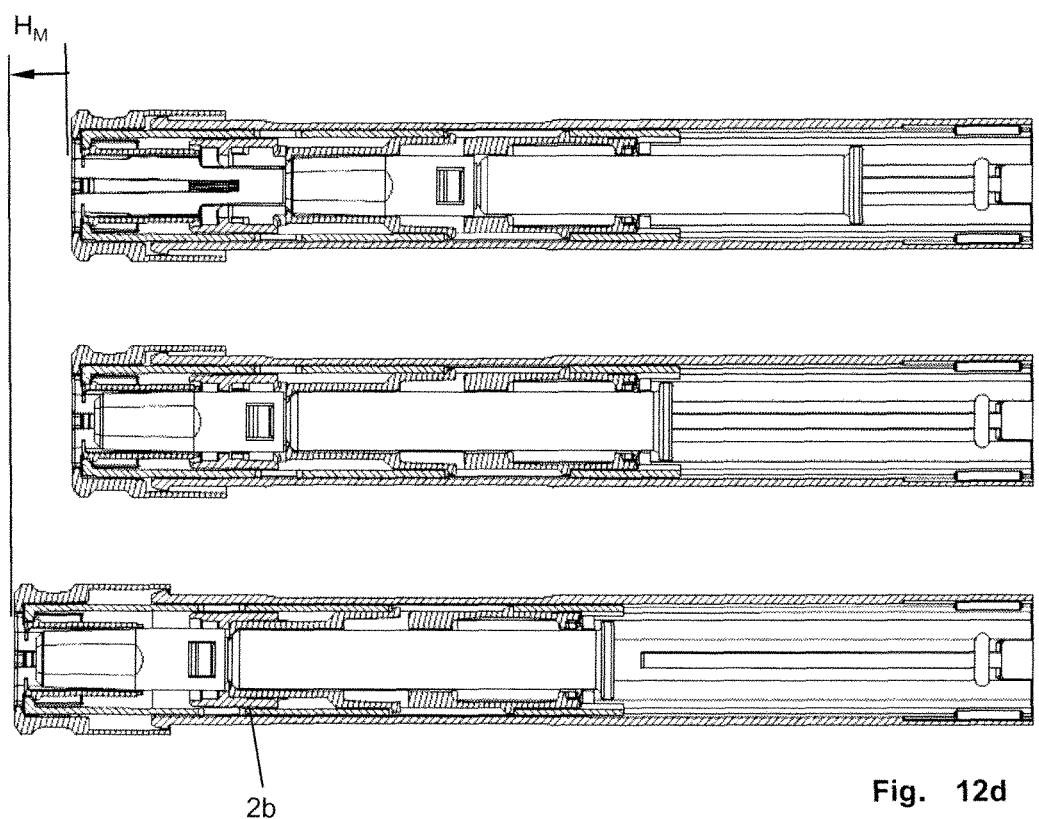

In this variant, the at least one engagement element can be formed elastically as a shoulder 1b, in particular, on an elastic arm 1h on the syringe holder, whereby the syringe 13 is inserted, through the proximal end with the needle pointing forward, into the syringe holder, which is preferably sleeve-shaped, whereby the needle protective cap 14 deflects outward the at least one engagement element 1b transverse to the longitudinal axis, i.e., away from the longitudinal axis, causing, if the needle protective cap 14 was moved completely past the at least one engagement element 1b, the at least one engagement element 1b to snap into the gap between the tapering area of the syringe 13 and the proximal end of the needle protective cap 14. The unit shown in FIG. 12c is then accommodated in the housing 2 of the autoinjector in such a way that the holding section 2b fixes the arm 1h such that the engagement elements 1b are held in engagement with the tapering section of the syringe body 13 in a force- or form-locking manner and no longer spring out of this engagement.

In FIGS. 8e, 9d, 10e, 11d, and 12d longitudinal sections of the five embodiments in the delivery state are shown, and for the embodiments two to five longitudinal sections are shown after one assembly step, respectively of the syringe into the autoinjector in one position each with a partially and completely inserted syringe. With a completely inserted syringe, the at least one snap 4b comprising the pull cap 4 also engages in the gap between the syringe body 13, in particular, in its tapering area, and the proximal end of the rigid needle shield 14 (FIG. 2a, 2b).

The at least one engagement element 1b is inserted into the area of the holding section 2b together with the syringe holder 1 by one installment stroke $H_M$, which, in particular, is performed as the last assembly step, in the axial direction so that a force- or form-locking connection results which prevents the at least one engagement element 1b from moving out of engagement with the tapering section of the syringe body 13 transverse to the longitudinal axis, in particular, away from the longitudinal axis L or outward. Further, by this installation stroke, the pull cap 4 is moved into its distal position, which it assumes in the delivery state of the autoinjector, whereby the pull cap 4 is moved through the syringe holder 1 by means of the at least one snap hook 4a which is supported on the syringe holder 1.

The invention claimed is:

1. An autoinjector for dispensing a liquid product, comprising:
    a housing;
    a product container arranged in the housing, the product container comprising a syringe and a displaceable piston for dispensing the product contained in the product container;
    a drive member for displacing the piston during the product dispensing;
    a first spring for displacing the drive member, wherein the first spring is pretensioned such that it can dispense the product from the product container by displacing the drive member and the piston by a dispensing stroke in a dispensing direction;
    a signal element;
    a signal stop; and
    a second spring,
    wherein the second spring exerts a spring force on the signal element opposite the dispensing direction, and
    wherein the signal element is releasably coupled with the drive member in an axial coupling such that, during and via the axial coupling, during a partial stroke of the dispensing stroke, the signal element is displaced in the dispensing direction as the drive member is displaced such that the second spring is tensed, and upon release of the axial coupling, the signal element is displaceable by the second spring opposite the dispensing direction and relative to one or more of the drive member or the housing to strike the signal stop of the housing to generate thereby one or more of an acoustic or a tactile signal.

2. The autoinjector according to claim 1, wherein the signal element comprises a first engagement element, which detachably engages the drive member in the axial coupling, wherein the axial coupling between the drive member and the signal element is released when the first engagement element is detached from engagement with the drive member.

3. The autoinjector according to claim 1, wherein the signal stop is formed axially fixedly connected to the housing.

4. The autoinjector according to claim 3, wherein the signal stop is configured as a locking cap for closing a proximal end of the housing.

5. The autoinjector according to claim 1, wherein the signal stop is arranged along a longitudinal axis of the housing and in alignment with the signal element.

6. The autoinjector according to claim 1, further comprising a needle protective sleeve for acting on the second spring and for triggering the product dispensing, wherein the needle protective sleeve is moveable from a starting position relative to the housing and along a longitudinal axis of the autoinjector in a proximal direction by an activation stroke, whereby the second spring is tensioned and dispensing of the product is triggered.

7. The autoinjector according to claim 6, further comprising a switch module arranged at least one of kinematically and geometrically between the second spring and the needle protective sleeve, wherein the switch module is transported in the proximal direction by the needle protective sleeve when the needle protective sleeve is displaced from the starting position in the proximal direction.

8. The autoinjector according to claim 7, wherein the signal element comprises:
    a first engagement element, which detachably engages the drive member and the signal element in the axial coupling; and
    a second engagement element, which can be moved into an axially fixed engagement with the needle protective sleeve or the switch module by a decoupling movement of the axial coupling between the drive member and the signal element,
    wherein the first engagement element and the second engagement element are coordinated with one another such that the second engagement element engages in the axially fixed engagement with the needle protective sleeve or the switch module when the first engagement element has not yet detached from the engagement with the drive member.

9. The autoinjector according to claim 8, wherein the drive member is moveable in a distal direction relative to the signal element by means of the first spring when the first engagement element is detached from the drive member, and the second engagement element is in engagement with the needle protective sleeve or the switch module.

10. The autoinjector according to claim 8, wherein the drive member prevents the second engagement element from moving out of the axially fixed engagement with the needle protective sleeve or with the switch module when the drive member moves in a distal direction relative to the signal element, wherein at the end of the dispensing stroke, the drive member allows the second engagement element to move out of engagement with the needle protective sleeve or with the switch module, whereby the signal element is accelerated by the second spring against the dispensing direction and strikes the signal stop.

11. The autoinjector according to claim 7, further comprising a holding element on which one end of the first spring is supported and which comprises a first engagement element, wherein the first engagement element engages the drive member before product dispensing is triggered, whereby the drive member is prevented from moving in the dispensing direction relative to the holding element, wherein said engagement of the first engagement element can be released for the product dispensing so that the first spring can move the drive member in the dispensing direction relative to the holding element.

12. The autoinjector according to claim 11, wherein the holding element comprises a second engagement element, which can be moved by a disengaging movement of the first engagement element of the holding element out of the drive member into an axially fixed engagement with the needle protective sleeve or the switch module, wherein the first engagement element of the holding element and the second engagement element of the holding element are coordinated with one another such that the second engagement element of the holding element engages the needle protective sleeve or the switch module in an axially fixed manner when the first engagement element of the holding element has not yet decoupled from the drive member.

13. The autoinjector according to claim 12, wherein the drive member prevents the second engagement element of the holding element from moving out of the axially fixed engagement with the needle protective sleeve or with the switch module when the drive member moves in a distal direction relative to the signal element and stops at the end of the dispensing stroke.

14. The autoinjector according to claim 13, wherein the switch module comprises a switch sleeve and a blocking sleeve, wherein the blocking sleeve comprises a unidirectionally acting locking element which engages the switch sleeve, wherein during movement relative to the housing in the proximal direction, the switch sleeve transports the blocking sleeve via the locking element, and during movement relative to the housing in the proximal direction, the blocking sleeve is moved into a further blocking position in which the locking element blocks a movement of the switch sleeve relative to the blocking sleeve in the proximal direction.

15. The autoinjector according to claim 6, wherein upon the drive member being displaced by the dispensing stroke in a distal direction, the needle protective sleeve can be moved by the second spring in the distal direction relative to the housing by a needle protective stroke into the needle protective position in which the needle protective sleeve protrudes distally beyond a needle tip of an injection needle of the product container.

16. The autoinjector according to claim 15, further comprising a locking element which blocks the needle protective sleeve in a needle protective position relative to the housing against being pushed back in the proximal direction such that the needle tip cannot protrude from a distal end of the needle protective sleeve.

17. The autoinjector according to claim 1, wherein the product container is accommodated in the housing so it cannot be moved along a longitudinal axis of the autoinjector.

18. An autoinjector for dispensing a liquid product, comprising:
   a housing;
   a product container arranged in the housing, the product container comprising a syringe and a displaceable piston for dispensing the product contained in the product container;
   a drive member for displacing the piston during the product dispensing;
   a first spring for displacing the drive member, wherein the first spring is pretensioned such that it can dispense the product from the product container by displacing the drive member and the piston by a dispensing stroke in a dispensing direction;
   a signal element;
   a signal stop arranged along a longitudinal axis of the housing and in alignment with the signal element; and
   a second spring,
   wherein the second spring exerts a spring force on the signal element opposite the dispensing direction,
   wherein the signal element is releasably coupled with the drive member in an axial coupling such that, during the axial coupling, the signal element is displaced in the dispensing direction as the drive member is displaced and the second spring is tensed, and upon release of the axial coupling, the signal element is displaceable by the second spring opposite the dispensing direction and relative to one or more of the drive member or the housing to strike the signal stop of the housing to generate thereby one or more of an acoustic or a tactile signal, and
   wherein upon the drive member being displaced by the dispensing stroke, a needle protective sleeve can be moved by the second spring in the distal direction relative to the housing by a needle protective stroke into a needle protective position in which the needle protective sleeve protrudes distally beyond a needle tip of an injection needle of the product container.

19. The autoinjector according to claim 18, wherein the needle protective sleeve is moveable from a starting position relative to the housing and along a longitudinal axis of the autoinjector in a proximal direction by an activation stroke, whereby the second spring is tensioned and dispensing of the product is triggered.

* * * * *